(12) United States Patent
Lamberti et al.

(10) Patent No.: US 9,128,076 B2
(45) Date of Patent: Sep. 8, 2015

(54) MEASUREMENT OF ISOTOPE RATIOS IN COMPLEX MATRICES

(75) Inventors: William A. Lamberti, Stewartsville, NJ (US); Hubert E. King, Flemington, NJ (US); William C. Horn, Long Valley, NJ (US); Mindy M. Zimmer, Los Alamos, NM (US); Gordon Macleod, Houston, TX (US); Robert J. Pottorf, Houston, TX (US); Leonard J. Srnka, Bellaire, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 141 days.

(21) Appl. No.: 13/641,658

(22) PCT Filed: Jan. 6, 2011

(86) PCT No.: PCT/US2011/020371
§ 371 (c)(1),
(2), (4) Date: Oct. 16, 2012

(87) PCT Pub. No.: WO2011/136858
PCT Pub. Date: Nov. 3, 2011

(65) Prior Publication Data
US 2013/0037707 A1    Feb. 14, 2013

Related U.S. Application Data

(60) Provisional application No. 61/329,990, filed on Apr. 30, 2010.

(51) Int. Cl.
*G01N 33/24*    (2006.01)
(52) U.S. Cl.
CPC .................................. *G01N 33/241* (2013.01)

(58) Field of Classification Search
USPC ............ 250/282, 288; 436/25–26, 29, 31–32, 436/173
See application file for complete search history.

(56) References Cited

U.S. PATENT DOCUMENTS

| 4,311,683 | A | 1/1982 | Hass et al. |
| 4,517,461 | A | 5/1985 | Crandall |

(Continued)

FOREIGN PATENT DOCUMENTS

| CN | 103364508 | 10/2013 |
| CN | 103592281 | 2/2014 |

(Continued)

OTHER PUBLICATIONS

Bakale, D. K. et al, Analytical Chemistry 1975, 47, 1532-1537.*

(Continued)

*Primary Examiner* — Arlen Soderquist
(74) *Attorney, Agent, or Firm* — ExxonMobil Upstream Research Company Law Dept.

(57) ABSTRACT

The present techniques are directed to a method for microprobe analyses of isotope ratios in inhomogeneous matrices. The method includes selecting matrix standards that have matrices that resemble a target matrix. A bulk isotope analysis is run on each of the matrix standards to determine a bulk isotope ratio value. A microprobe analysis is run on each of the matrix standards to determine a microprobe isotope ratio values for each of the plurality of matrix standards. Spurious values are eliminated from the microprobe isotope ratio values. The microprobe isotope ratio values are averaged for each of the matrix standards to create an average microprobe isotope ratio value associated with each of the matrix standards. The bulk isotope ratio value for each of matrix standards is plotted against the average microprobe isotope ratio value associated with each of the matrix standards to create a matrix corrected calibration curve.

33 Claims, 10 Drawing Sheets

(56) References Cited

U.S. PATENT DOCUMENTS

| | | | |
|---|---|---|---|
| 4,558,014 A | | 12/1985 | Hirschfeld et al. |
| 4,856,351 A | | 8/1989 | Smith et al. |
| 4,898,831 A | * | 2/1990 | Smith ............................ 436/32 |
| 4,960,567 A | | 10/1990 | Smith |
| 4,965,209 A | * | 10/1990 | Smith ............................ 436/32 |
| 5,012,052 A | | 4/1991 | Hayes |
| 5,049,738 A | | 9/1991 | Gergely et al. |
| 5,087,815 A | | 2/1992 | Schultz et al. |
| 5,241,859 A | | 9/1993 | Smith |
| 5,286,651 A | * | 2/1994 | Smith ............................ 436/32 |
| 5,328,849 A | * | 7/1994 | Smith ............................ 436/32 |
| 5,416,024 A | * | 5/1995 | Smith ............................ 436/32 |
| 5,898,174 A | * | 4/1999 | Franzen ....................... 250/287 |
| 5,969,348 A | * | 10/1999 | Franzen ....................... 250/282 |
| 6,393,906 B1 | | 5/2002 | Vityk et al. |
| 6,437,325 B1 | * | 8/2002 | Reilly et al. ............... 250/252.1 |
| 6,519,542 B1 | * | 2/2003 | Giannuzzi et al. .............. 702/85 |
| 6,661,000 B2 | | 12/2003 | Smith et al. |
| 7,173,242 B2 | | 2/2007 | Liu et al. |
| 7,210,342 B1 | | 5/2007 | Sterner et al. |
| 7,395,691 B2 | | 7/2008 | Sterner et al. |
| 7,425,694 B2 | * | 9/2008 | Nishizawa et al. ........... 250/207 |
| 2002/0013687 A1 | | 1/2002 | Ortoleva |
| 2002/0120429 A1 | | 8/2002 | Ortoleva |
| 2007/0267565 A1 | * | 11/2007 | Nishizawa et al. ........... 250/207 |
| 2009/0050369 A1 | | 2/2009 | Pop et al. |
| 2010/0024686 A1 | | 2/2010 | Constantz et al. |
| 2010/0155078 A1 | | 6/2010 | Walters et al. |
| 2012/0215447 A1 | | 8/2012 | Lin |
| 2013/0125674 A1 | | 5/2013 | Zhang et al. |
| 2013/0327643 A1 | | 12/2013 | Rostro et al. |

FOREIGN PATENT DOCUMENTS

| | | |
|---|---|---|
| CN | 103712841 | 4/2014 |
| CN | 103940804 | 7/2014 |

OTHER PUBLICATIONS

Galuska, A. A. et al, Analytical Chemistry 1984, 56, 74-77.*
Summers, W. R. et al, Analytical Chemistry 1986, 58, 2126-2129.*
Brenan, J. M. et al, Geochimica et Cosmochimica Acta 1995, 59, 3331-3350.*
Riciputi, L. R., Rapid Communications in Mass Spectrometry 1996, 10, 282-286.*
Mojzsis, S. J. et al, Nature 1996, 384, 55-59.*
Graham, C. M. et al, Geochimica et Cosmochimica Acta 1996, 60, 5101-5116.*
Paterson B. A. et al, Geochimica et Cosmochimica Acta 1997, 61, 601-609.*
Eller, J. M. et al, Chemical Geology 1997, 138, 221-244.*
McKeegan, K. D. et al, Science 1998, 280, 414-418.*
Riciputi, L. R. et al, International Journal of Mass Spectrometry 1998, 178, 65-71.*
Mahon, K. I. et al, Chemical Geology 1998, 152, 227-256.*
Mahon, K. I. et al, Chemical Geology 1998, 152, 257-271.*
Ripperdan, R. L. et al, Journal of Geophysical Research 1998, 103, 21015-21023.*
Upton, B. G. J. et al, Journal of Petrology 1999, 40, 935-956.*
Haszeldine, R. S. et al, Journal of Geochemical Explorations 2000, 69-70, 195-200.*
Ottolini, L. P., Microchimica Acta 2000, 132, 467-478.*
Spotl, C. et al, in Quartz Cementation in Sandstones, R. H Worden et al, Ed. Special Publications of the International Association of Sedimentologists 2000, 29, 281-297.*
Lyon, I. C. et al, in Quartz Cementation in Sandstones, R. H Worden et al, Ed. Special Publications of the International Association of Sedimentologists 2000, 29, 299-316.*
Girard, J.-P. et al, Chemical Geology 2001, 176, 73-92.*
Hirata, T., Analytical Chemistry 2003, 75, 228-233.*
Valley, J. W. et al, Geochimica et Cosmochimica Acta 2003, 67, 3257-3266.*
Rollion-Bard, C. et al, Coral Reefs 2003, 22, 405-415.*
Buschaert, S. et al, Applied Geochemistry 2004, 19, 1201-1215.*
Layne, G. D. et al, Chemical Geology 2004, 207, 277-289.*
Godon, A. et al, Chemical Geology 2004, 207, 291-303.*
Fletcher, I. R. et al, Chemical Geology 2004, 209, 295-314.*
Papineau, D. et al, Geochimica et Cosmochimica Acta 2005, 69, 5033-5060.*
Kelly, J. L. et al, Geochimica et Cosmochimica Acta 2007, 71, 3812-3832.*
Eiler, J. M. et al, Geochemistry Geophysics Geosystems 2007, 8, 21 pages.*
Sano, Y. et al, Applied Geochemistry 2008, 23, 2406-2413.*
Kita, N. T. et al, Chemical Geology 2009, 264, 43-57.*
Li, X.-H. et al, Geochemistry Geophysics Geosystems 2009, 10, 21 pages.*
Page, F. Z. et al, Chemical Geology 2010, 270, 9-19.*
Rodushkin, I. et al, Journal of Analytical Atomic Spectrometry 2002, 17, 1231-1239.*
N. E. Aase, and O. Walderhaug, *The Effect of Hydrocarbons on Quartz Cementation: Diagenesis in the Upper Jurassic Sandstones of the Miller Field, North Sea, Revisited*, 11 Petroleum Geoscience 215-223 (2005).
I. R. Fletcher, M. R. Kilburn, and B. Rasmussen, 2008, *Nanosims Mu µ-Scale In Situ Measurement of C-13/C-12 in Early Precambrian Organic Matter, with Permil Precision*, 278 International Journal of Mass Spectrometry 59-68.
C. I. Macaulay, A. E. Fallick, R. S. Haszeldine, and C. M. Graham, *Methods of Laser-Based Stable Isotope Measurement Applied to Diagenetic Cements and Hydrocarbon Reservoir Quality*, 35 Clay Minerals 313-322 (2000).
A. M. E. Marchand, C. I. Macaulay, R. S. Haszeldine, and A. E. Fallick, *Pore Water Evolution in Oilfield Sandstones: Constraints from Oxygen Isotope Microanalyses of Quartz Cement*, 191 Chemical Geology 285-304 (2002).
Sharp, Z., Principles of Stable Isotope Geochemistry (Pearson Prentice Hall, Upper Saddle River, NJ, 2007), pp. 31-35.
C. Spotl and D. Mattey, *Stable Isotope Microsampling of Speleothems for Palaeoenvironmental Studies: A Comparison of Microdrill, Micromill and Laser Ablation Techniques*, 235 Chemical Geology 48-58 (2006).
Vincent, B., L. Emmanuel, P. Houel, and J. Loreau, *Geodynamic Control on Carbonate Diagenesis: Petrographic and Isotopic Investigation of the Upper Jurassic Formations of the Paris Basin (France)*, 197 Sedimentary Geology 267-289 (2007).

\* cited by examiner

100

200

300

900

1000

1100

1200

Bitumen 05DH046

1300

1400

MEASUREMENT OF ISOTOPE RATIOS IN COMPLEX MATRICES

CROSS-REFERENCE TO RELATED APPLICATION this application is the National Stage of International Application No. PCT/US2011/020371, filed 6 Jan. 2011, which claims the benefit of U.S. Provisional Patent Application No. 61/329,990 filed 30 Apr. 2010 entitled MEASUREMENT OF ISOTOPE RATIOS IN COMPLEX MATRICES, the entirety of which is incorporated by reference herein.

TECHNICAL FIELD

Exemplary embodiments of the present techniques relate to a method and system for determining isotope ratios of materials in complex matrices.

BACKGROUND

Accurate determination of geological history in a region or sub-region of a hydrocarbon-bearing province is important in order to build basin-scale, play-scale, and reservoir-scale models of potential hydrocarbon targets. Predictions of oil and gas yields as well as reservoir porosity and permeability are important for assessing hydrocarbon resources. These quantities may be dependent on the thermal and chemical history of a reservoir over geological time. For example, the quality, quantity, and timing of the hydrocarbon may be influenced by the pressures and temperatures to which the source rocks, components thereof, migration pathways, and reservoirs have been subjected. Consequently, models for these properties are important tools for locating and harvesting hydrocarbon reservoirs.

Further, the isotopic signatures of the materials that make up reservoir rocks (such as the minerals, fluids, fossils, and hydrocarbons) reflect their respective geologic, chemical, and biological histories. Such information can be of great relevance to petroleum exploration, production, and development. More specifically, as the rocks are altered in the reservoir, the minerals making up the rocks can attain various isotopic signatures that are uniquely tied to the conditions at the time of the alteration. The resulting signatures may be "frozen" into the sample as the minerals solidify. As the grains age over geologic timescales, the original solidified minerals can be covered by overlayers with other isotopic signatures, indicative of conditions different from those already "frozen" into the interior portions of the grain.

For example, U.S. Pat. No. 4,517,461 to Crandall discloses a carbon isotope analysis of hydrocarbons. The method involves the introduction of a sample containing an isotope of interest into an analytical detector operative to convert the sample into a product analyzable by a mass spectrometer. A property of the sample representative of the quantity of at least one of its constituents is detected, and the conversion product is passed from the detector to a mass spectrometer operative to detect the isotopic ratio of interest. The method optionally includes passing the sample or a source material through a chromatograph column for separation into suitable fractions. The apparatus includes an appropriate analytical detector and a mass spectrometer with optional chromatography column. The method and instrument are particularly suited for analysis of oil-related samples such as crude oil fractions, natural gas, soil gas and oil shale as a tool in oil prospecting.

A number of techniques have been used to analyze the isotope ratios of reservoir samples. These techniques have included, for example, conventional rock analysis, microdrilling or micromilling analysis, laser ablation techniques, and secondary ion mass spectrometry.

In conventional rock analysis, a significant quantity (for example, milligrams to tens of milligrams) of a material is separated from a rock. The separated sample is presumed to be a single type of material, for example, having a relatively uniform matrix. The separated sample is then chemically processed to produce a material for introduction into a mass spectrometer, for example, being dissolved in an acid. The chemically processed sample may be aspirated into a stream of gas that is introduced into the instrument. The chemically processed sample may be ionized during introduction, for example, by being converted to a plasma in this introduction step. Highly accurate values of the isotope ratios may then be determined for the sample.

For example, U.S. Pat. No. 5,012,052 to Hayes discloses an apparatus and method for isotope-ratio-monitoring by gas chromatography-mass spectrometry. With the apparatus and method, samples are introduced in a hydrogen carrier gas into a gas chromatograph and resolved into discrete compounds. The discrete compounds are thereafter introduced to a selectively permeable membrane separator, employing palladium, palladium alloy or other suitable material, to separate out the hydrogen carrier. A replacement carrier gas is simultaneously introduced to carry the chromatographic sample to a combustion reactor, water separator and isotope-ratio-monitoring mass spectrometer. The replacement carrier gas is introduced at a lower flowrate than the hydrogen carrier gas, thus permitting lower flowrates to be introduced to the mass spectrometer to improve its precision. Flowrates to the mass spectrometer are thus reduced without any loss or fractionation of the sample. An improved combustion system is employed to reduce system volume and equalize system pressure, while still providing quantitative combustion.

The traditional use of this method has demonstrated the utility of this information to determine the geologic history of bulk samples. However, due to the quantity of the material used in the analysis, contamination with unwanted materials, for example, materials having other matrices, may be a problem. Separation of the materials prior to chemical processing can be time-consuming and therefore costly. Further, the chemical processing of materials prior to introduction into the mass spectrometer is time consuming, requiring highly specialized analytical chemical skills. See Sharp, Z., PRINCIPLES OF STABLE ISOTOPE GEOCHEMISTRY (Pearson Prentice Hall, Upper Saddle River, N.J., 2007).

In micromilling (or microdrilling) analysis, a small quantity of powder is produced by mechanical abrasion of a target region in a sample, providing spatial resolution and reducing potential contamination versus bulk analysis. The resulting analyzed volume may be cylindrical or trench shaped, depending on the tool used. The minimum volume of material that can be sampled using this technique is approximately $10^8$ $\mu m^3$, which may be equivalent to a fraction of a milligram of material. The size of the micromill or microdrill tool determines the minimum step size resolution, with values as small as 100 µm reported.

However, rock components of interest may be smaller than the minimum spatial resolution for this method. See Vincent, B., L. Emmanuel, P. Houel, and J. Loreau, *Geodynamic Control on Carbonate Diagenesis: Petrographic and Isotopic Investigation of the Upper Jurassic Formations of the Paris Basin* (France), 197 SEDIMENTARY GEOLOGY 267-289 (2007). Further, chemical processing of the resulting powder requires time consuming specialized analytical chemical skills, due to the small sample size. As a result, microdrilling or micromilling may be used more often on carbonate-based rock components than on materials having other matrices, as carbonate matrices are softer and more easily dissolved than many other matrices. See C. Spotl and D. Mattey, *Stable Isotope Microsampling of Speleothems for Palaeoenvironmental Studies: A Comparison of Microdrill, Micromill and Laser Ablation Techniques*, 235 CHEMICAL GEOLOGY 48-58 (2006) (hereinafter "Spotl").

In laser spectrometry, a focused laser beam can provide spatial analysis with typical spot sizes of about 100 μm. Three methods may be used to sample the material: laser ablation, thermal vaporization, and chemical reaction. In laser ablation, material can be directly removed from the surface of the sample and ionized by the energy from the photons in the laser. The ionized material may be captured by a radio wave generated plasma and released into a induction stream into a mass spectrometer, for example, in techniques such as laser ablation inductively coupled plasma mass spectrometry (laser ablation-ICP-MS). In another technique, the laser may be used as a direct source of heat energy to the surface of the sample, causing vaporization of the sample at a target point. The vaporized material may then be captured in a neutral gas induction stream and fed into a mass spectrometer. In chemical reaction techniques, the laser may energize a reactive gas at the surface of the sample, causing the formation of a corrosive ionized atmosphere in a target area.

However, laser based methods generally require specialized lasers, with frequencies tailored to either the characteristics of the solid sample or to the solid's reaction with a reactive gas environment. Therefore, to analyze a full suite of rock components can require several specialized instruments. Further, a correction to account for mass fractionation during sample generation, specific to that isotope and solid, must be applied. The spatial resolution is significantly larger than the beam size due to beam damage, which is 2-to-4 times the diameter of the beam. See Spotl; C. I. Macaulay, A. E. Fallick, R. S. Haszeldine, and C. M. Graham, *Methods of Laser-Based Stable Isotope Measurement Applied to Diagenetic Cements and Hydrocarbon Reservoir Quality*, 35 CLAY MINERALS 313-322 (2000).

In secondary ion mass spectrometry (SIMS), a focused ion beam sputters material from a surface of a sample, ejecting ionized particles, which are then introduced into an attached mass spectrometer for analysis. Spot sizes for typical isotopic analysis range in size from several tens of μm in diameter down to 3×3 μm². The technique is efficient, requiring less than $10^2$ μm³ of material, corresponding to a few nanograms. Although any solid component may be analyzed, variations in the matrices will be reflected in different measured isotope ratios. This is a result of the slight differences in reactivity exhibited by different isotopes of an element. Thus, a matrix correction may be required to provide accurate results. There are several empirical schemes to calculate matrix corrections, but these may not be sufficiently accurate for quantitative geochemistry.

Application of SIMS analysis to rock analysis has been tested by a few groups. For example, one study performed SIMS based on a single matrix correction that did not take into account the effects of variation of compositional changes. See I. R. Fletcher, M. R. Kilburn, and B. Rasmussen, 2008, *Nanosims Mu μ-Scale In Situ Measurement of C-13/C-12 in Early Precambrian Organic Matter, with Permil Precision*, 278 INTERNATIONAL JOURNAL OF MASS SPECTROMETRY 59-68. Although the technique has a high spatial resolution, the full advantages of the theoretical limits have not been realized, and as a consequence, thin microquartz rims were missed in some analyses of oxygen isotopes. See A. M. E. Marchand, C. I. Macaulay, R. S. Haszeldine, and A. E. Fallick, *Pore Water Evolution in Oilfield Sandstones: Constraints from Oxygen Isotope Microanalyses of Quartz Cement*, 191 CHEMICAL GEOLOGY 285-304 (2002); N. E. Aase, and O. Walderhaug, *The Effect of Hydrocarbons on Quartz Cementation: Diagenesis in the Upper Jurassic Sandstones of the Miller Field, North Sea, Revisited*, 11 PETROLEUM GEOSCIENCE 215-223 (2005).

Although the use of microanalytic techniques is widespread, these techniques are seldom applied to problems associated with the reservoir rocks of hydrocarbon reservoirs. The predominant applications of the prior microanalytical techniques to natural samples are in characterizing mantle geochemistry, cosmochemistry, paleo-oceanography, and age dating. Isotopic and trace element chemistry is often used for mantle geochemistry. The use of microanalytics for cosmochemistry is driven by the fact that sample sizes are nearly always limited and the geochemical questions are closely related to mantle geochemistry. The interest of the paleo-oceanographers is driven by interest in global climate change.

SUMMARY

An exemplary embodiment of the present techniques provides a method for microprobe analyses of isotope ratios in inhomogeneous matrices. The method includes selecting a plurality of matrix standards that have matrices that have a common characteristic with a target matrix. A bulk isotope analysis is run on each of the plurality of matrix standards to determine a bulk isotope ratio value for each of the plurality of matrix standards. A plurality of microprobe analyses is run on each of the plurality of matrix standards to determine a plurality of microprobe isotope ratio values for each of the plurality of matrix standards. Spurious values are eliminated from the plurality of microprobe isotope ratio values and the plurality of microprobe isotope ratio values for each of the plurality of matrix standards are averaged to create an average microprobe isotope ratio value associated with each of the plurality of matrix standards. The bulk isotope ratio value for each of the plurality of matrix standards is plotted against the average microprobe isotope ratio value associated with each of the plurality of matrix standards to create a matrix corrected calibration curve.

A working standard may be run at each analysis to correct isotope ratio measurements for instrumental mass fractionation (IMF). The method may include creating a map of isotope ratios of the sample matrix. The method may include determining a quality of a reservoir core sample. A map of grain coatings may be created from the map of isotope ratios. A map of cements may be created from the map of isotope ratios.

The map may include $^{13}C/^{12}C$ ($\delta^{13}C$) ratios. The method may include determining an origin of carbon in minerals in the sample matrix.

The map may include $^{18}O/^{16}O$ ($\delta^{18}O$) ratios. The method may include determining a temperature of precipitation for minerals in the sample matrix.

The map may include $^{34}S/^{32}S$ ($\delta^{34}S$) ratios. The method may include determining an origin of sulfur in minerals in the sample matrix.

The method may include determining grain provenance from the map of isotope ratios. The sample matrix may be frozen on a cryogenic stage to solidify fluids in the sample matrix prior to creating the map of isotope ratios of the sample matrix comprising the fluids. The method may include determining a connectivity of the sample matrix.

Another exemplary embodiment provides a method for analyzing the potential of a hydrocarbon reservoir. The method includes obtaining a rock sample from the hydrocarbon reservoir and selecting a plurality of matrix standards that have matrices that have a common characteristic with the rock sample. A bulk isotope analysis is run on each of the plurality of matrix standards to determine a bulk isotope ratio value for each of the plurality of matrix standards. A plurality of microprobe analyses is run on each of the plurality of matrix standards to determine a plurality of microprobe isotope ratio values for each of the plurality of matrix standards. Spurious values are eliminated from the plurality of microprobe isotope ratio values. The plurality of microprobe isotope ratio values for each of the plurality of matrix standards are averaged to create an average microprobe isotope ratio value associated with each of the plurality of matrix standards. The bulk isotope ratio value for each of the plurality of matrix standards is plotted against the average microprobe isotope ratio value for each of the plurality of matrix standards to create a matrix corrected calibration curve. A microprobe analysis is run on a target region of the rock sample and the matrix corrected calibration curve is used to determine an isotope ratio, $\delta''M$, for a selected element in the target region.

A size of the target region may be less than about 0.8 $\mu m^3$. The microprobe technique may include secondary ion mass spectrometry (SIMS) or atom-probe mass spectrometry.

The method may include determining the isotope ratios ($\delta''M$), of a fluid inclusion in the rock by: solidifying the fluid inclusion using a low temperature; and running a microprobe analysis on the solidified fluid inclusion. An isotope ratio of components in a frozen brine in the solidified fluid inclusion may be determined.

A thermal, chemical and/or physical condition of a rock sample may be determined based at least in part on the isotope ratio for the selected element. Hydrocarbons may be produced from the potential hydrocarbon reservoir based at least in part on the thermal, chemical and/or physical condition of the rock sample. The isotope ratio may be a $^3C/^{12}C$ isotope ratio ($\delta^{13}C$), and the method may includes determining a carbonate diagenesis based, at least in part, on the $\delta^{13}C$.

The isotope ratio may be a $^{18}O/^{16}O$ isotope ratio ($\delta^{18}O$). A temperature of formation for silica cement may be determined based, at least in part, on the $\delta^{18}O$. The method may include obtaining a record of formation temperature for the target region from a paleothermometer, determining a salinity of a fluid trapped in the target region, and determine a pore fluid evolution based at least in part on the $\delta^{18}O$, a fractionation factor for a mineral-water pair, and the formation temperatures.

The isotope ratio may be a $^{34}S/^{32}S$ isotope ratio ($\delta^{34}S$). The method may include determining the probability of a sour gas condition based at least in part on the $\delta^{34}S$. Further, the method may include dating the time of precipitation of the target region based at least in part on a comparison of the $\delta^{34}S$ with a sulfur isotope variation in seawater over a period of time. The method may include determining an origin for $H_2S$ in a reservoir by comparing the $\delta^{34}S$ of a gas in the reservoir to the $\delta^{34}S$ of the target region, and modifying exploration strategies based on a location of a sulfate source for the $H_2S$.

The isotope ratio may be a $^{87}Sr/^{86}Sr$ isotope ratio ($\delta^{86}Sr$) of a Ca-bearing cement, and the method may include determining an origin and precipitation time for a cement by comparing the $\delta^{86}Sr$ to a curve showing isotope variation over time.

Another exemplary embodiment of the present techniques provides a system for analyzing isotope variations in inhomogeneous matrices The system includes an ion generator configured to generate ions from a target region of a sample. The system also includes a particle detector configured to generate a signal that is proportional to the number of isotopes for a target element in the target region. An analysis unit in the system may include an input system configured to process the signal from the particle detector to determine a count for two or more isotopes for the target element, a processor, and a memory device. The memory device may include code configured to direct the processor to: calculate an isotope ratio for the target element, project the isotope ratio onto a matrix corrected calibration curve, and determine a matrix corrected value for the isotope ratio. The system may include a sector field mass spectrometer and/or an atom probe.

BRIEF DESCRIPTION OF THE DRAWINGS

The advantages of the present techniques are better understood by referring to the following detailed description and the attached drawings, in which.

DETAILED DESCRIPTION

Figure 1:
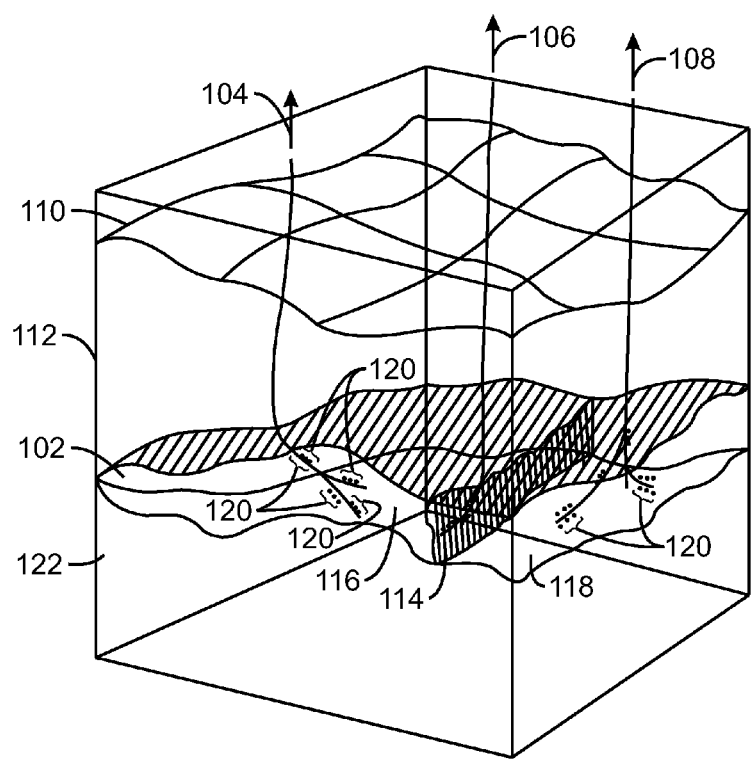
FIG. 1 is a schematic view of a reservoir, in accordance with an exemplary embodiment of the present techniques.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

"Brine" is an aqueous solution containing a relatively high concentration of monovalent, divalent or trivalent metallic cations such as those of iron, aluminum, calcium, magnesium, sodium or potassium. Brine solutions contain, for example, from about 200 to about 200,000 weight parts per million weight parts water of divalent cation, and/or about 500 to about 500,000 ppm monovalent cation. Brines include solutions of alkali or alkaline earth metal salts in solution in water and whose salt concentration can vary up to nearly saturated. These salts include, among others, alkali metal or alkaline earth chlorides, bromides, sulfates, hydroxides, nitrates, and the like and natural brines. Brine sources include natural brines as Chilean brines, geothermal brines, sea water, mineral brines such as LiCl brine, KCl brine, other alkali metal salt brines and industrial brines such as those recovered from ore leaching, mineral dressing, and the like.

"Clastic rocks" are rocks that are composed of fragments, or clasts, of pre-existing rock. The term is most commonly, but not uniquely, applied to sedimentary rocks, such as sandstone. Grain size determines the basic name of a clastic sedimentary rock. Grain size can vary from clay in shales and claystones, through silt in siltstones, sand in sandstones, and gravel, cobble, to boulder sized fragments in conglomerates and breccias.

As used herein, "carbonate" refers to carbonate rock (which is made of chiefly carbonate minerals). Both carbonate rock and carbonate mineral are primarily comprised of carbonate ion, $CO_2^3$. Carbonate minerals common in chemically-precipitated sedimentary rock. The most common are calcite or calcium carbonate, $Ca_3(CO_3)_2$, the chief constituent of limestone. This corresponds to the main component of mollusk shells and coral skeletons, from which carbonates often form. Other carbonate minerals include dolomite, a mineral comprised of calcium-magnesium carbonate $CaMg(CO_3)_2$, and siderite, comprised of iron (II) carbonate, $Fe_3(CO_3)_2$.

A "calibration curve" is a plot of how an instrumental response changes with a concentration of an analyte (the substance to be measured). As used herein, a calibration curve is a plot of an isotope ratio for a bulk sample against the measured isotope ratio for a rock sample having a particular matrix.

As used herein, "cement" indicates a mineral matrix that ties one or more types of rock or mineral fragments together to form a single entity. The properties of the cement may be used to evaluate the ability of a formation to trap or produce hydrocarbons.

"Cryogenic temperature" refers to one or more temperatures that are −50° C. or below.

"Connectivity" refers to a measure of the communication (or lack thereof) between points within a geologic zone. Connectivity is closely related to the reservoir internal geometry and is commonly a primary factor controlling hydrocarbon production efficiency and ultimate recovery.

As used herein, "diagenesis" is any chemical, physical, or biological change undergone by a sediment after deposition, outside of surface alteration (weathering) and metamorphism. Diagenesis occurs at relatively low temperatures and pressures and results in changes to the rock's original mineralogy and texture. Although diagenesis is usually reserved for changes to inorganic materials, the term may also be used to describe chemical, physical, or biological changes that form subsurface hydrocarbon deposits from carbon sources.

A "formation" is a subsurface region, regardless of size, comprising an aggregation of subsurface sedimentary, metamorphic and/or igneous matter, whether consolidated or unconsolidated, and other subsurface matter, whether in a solid, semi-solid, liquid and/or gaseous state, related to the geological development of the subsurface region. A formation may contain numerous geologic strata of different ages, textures and mineralogical compositions. A formation can refer to a single set of related geologic strata of a specific rock type or to a whole set of geologic strata of different rock types that contribute to or are encountered in, for example, without limitation, (i) the creation, generation and/or entrapment of hydrocarbons or minerals and (ii) the execution of processes used to extract hydrocarbons or minerals from the subsurface. A formation may include a reservoir, or may include rock layers above or below the reservoir.

"Fluid inclusions" are microscopic bubbles of liquid and/or gas that are trapped within minerals. As minerals often form in the presence of a liquid or aqueous medium, tiny amounts of that liquid can become trapped within the mineral structure. These small inclusions may range in size from 0.1 to 1 mm and are often only visible in detail by microscopic study.

"Hydrocarbon extraction" or "extracting hydrocarbons" includes planning the location and timing of new wells, drilling wells, removing hydrocarbons from a hydrocarbon reservoir, managing production from existing wells, predicting production lifetimes of wells or hydrocarbon reservoirs at various extraction rates, and other similar activities.

"Hydrocarbon management" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

"Hydrocarbon production" or extraction refers to any activity associated with extracting hydrocarbons from a well or other opening. Hydrocarbon production normally refers to any activity conducted in or on the well after the well is completed. Accordingly, hydrocarbon production or extraction includes, not only primary hydrocarbon extraction, but also secondary and tertiary production techniques, such as injection of gas or liquid for increasing drive pressure, mobilizing the hydrocarbon or treating. This may include the use of chemicals or hydraulic fracturing the well bore to promote increased flow, well servicing, well logging, and other well and wellbore treatments.

"Hydrocarbon reservoirs" include those containing any hydrocarbon substance, including for example one or more than one of any of the following: oil (often referred to as petroleum), natural gas, gas condensate, tar and bitumen. The following detailed description of various embodiments is presented with primary reference to oil reservoirs, but the principles discussed apply also to situations involving reservoirs containing other hydrocarbon materials, either in addition to oil or instead of oil.

"Hydrocarbons" may be produced from hydrocarbon formations through wells penetrating a hydrocarbon containing formation. "Hydrocarbons" are generally defined as molecules formed primarily of carbon and hydrogen atoms such as oil and natural gas. Hydrocarbons may also include other elements, such as, but not limited to, halogens, metallic elements, nitrogen, oxygen and/or sulfur. Hydrocarbons derived from a reservoir formation may include, but are not limited to, kerogen, bitumen, pyrobitumen, asphaltenes, oils or combinations thereof Hydrocarbons may be located within or adjacent to mineral matrices within the earth. Matrices may include, but are not limited to, sedimentary rock, sands, silicilytes, carbonates, diatomites and other porous media.

As used herein, an "ion" is an atom or molecule in which the total number of protons does not equal the total number of electrons. An ion beam is an accelerated stream of charged particles, usually charged atoms, that may be aimed at a surface to remove material for analysis.

As used herein, an "ion generator" is a device that is used to create a beam of charged particles or ions. The charged particles may be used to sample a surface in secondary ion mass spectrometers, atom probes, and the like.

As used herein, an "particle detector" is a device for counting neutral or charged particles. The particle detector may be used in an mass spectrometer, atom probe, or other device intended to accurately measure the mass of a molecule or atom.

"Isotopes" are atoms of the same chemical element that have different numbers of neutrons. The difference is weight may lead to minor differences in reactivity, which could present as mass fractionation during analyses. An isotope ratio may be measured as the ratio of two different isotopes of a single element in a sample.

"Matrices" include the materials that form a rock sample, including, but not limited to, sedimentary rock, sands, silicilytes, carbonates, diatomites, and other porous media.

"Organic-matter-rich rocks" ("ORRs") are accumulations of organic matter of photosynthetic-protist and bacterial origin that survived the processes of deposition and burial to be incorporated in rock strata. The deposition of ORRs and their ultimate source-rock quality are controlled by three sets of competing proximate controls: production, destruction, and dilution. The processes that control ORR accumulation cannot be detected or measured directly from the remote sensing data (e.g., seismic, well logs) typically available in exploration settings. Organic-rich rock formations include, for example, oil shale formations, coal formations, and tar sands formations. Rock matrices may include, but are not limited to, sedimentary rocks, shales, siltstones, sands, silicilytes, carbonates, and diatomites.

A "paleothermometer" is a methodology for determining past temperatures using a proxy found in a natural record such as a sediment, ice core, tree rings or a cell membrane composition. For example, $^{18}O:^{16}O$ ratios may be used as a proxy for temperature. The isotope ratio is presented as a shift in isotope ratios from a standard sample, $\delta^{18}O$, and is in given as "per mil," e.g., ‰, or parts per thousand, and may be defined by the formula shown in Eqn. 1.

$$\delta^{18}O = \left( \frac{\left(\frac{^{18}O}{^{16}O}\right)_{sample}}{\left(\frac{^{18}O}{^{16}O}\right)_{standard}} - 1 \right) * 1000 \, o/oo \qquad \text{Eqn. 1}$$

In Eqn. 1, the standard has a known isotope composition, such as Vienna Standard Mean Ocean Water (VSMOW).

"Pore volume" (PV) is defined as the volume of fluid associated with a portion of a reservoir. It is the product of average porosity and the volume of the portion of the reservoir in question.

"Reservoir data" may comprise various static characteristics of a reservoir, including structure components, such as geometric form and closure, depth, fault style and timing, dips, and compartmentalization, among others. Other reservoir data includes reservoir architecture components, such as depositional system, depositional environment, net-to-gross ratio, vertical heterogeneity, and interval thicknesses, among others. Further data includes rock type components, such as lithological components and pay distributions, among others. Reservoir data also include petrophysical components, such as fluid type, contacts, lateral permeability heterogeneity, vertical-to-horizontal permeability ratios, and diagenetic and mineralogical issues, among others.

"Reservoir formations" are typically pay zones (i.e., hydrocarbon production zones) that may include sandstone, limestone, chalk, coal and some types of shale. Pay zones can vary in thickness from less than one foot (0.3048 m) to hundreds of feet (hundreds of m). The permeability of the reservoir formation provides the potential for production.

"Reservoir model" or "simulation model" refer to a specific mathematical representation of a real hydrocarbon reservoir, which may be considered to be a particular type of geologic model. Simulation models are used to conduct numerical experiments regarding future performance of the field with the goal of determining the most profitable operating strategy. An engineer managing a hydrocarbon reservoir may create many different simulation models, possibly with varying degrees of complexity, in order to quantify the past performance of the reservoir and predict its future performance.

"Reservoir properties" and "reservoir property values" are defined as quantities representing physical attributes of rocks containing reservoir fluids, and may be one type of reservoir data, as discussed above. The term "reservoir properties" as used in this application includes both measurable and descriptive attributes. Examples of measurable reservoir property values include rock-type fraction (e.g., net-to-gross, v-shale, or facies proportion), porosity, permeability, water saturation, and fracture density. Examples of descriptive reservoir property values include facies, lithology (e.g., sandstone or carbonate), and environment-of-deposition (EOD). Reservoir properties may be populated into a reservoir framework to generate a reservoir model.

"Rock" and "hard rock" means any stiff reservoir rock characterized by high velocity and high density. In other words, hard rock means rocks whose acoustic response is controlled primarily by the rock frame and is relatively insensitive to fluid saturation change and pressure change due to hydrocarbon production. Non-limiting examples of hard rock include various carbonate or carbonate-type rocks and deep siliciclastic rocks.

"Sedimentary rock" refers generally to rock formed by the accumulation and cementation of mineral grains transported by wind, water, or ice to the site of deposition or chemically precipitated at the depositional site. The sedimentary rocks specific to this invention include reservoir rocks, source rocks, and conduit rocks.

A "siliciclastic rock" is a rock composed of fragments or portions of silicates. For example, sandstone is a siliciclastic rock.

"Salinity" refers to an amount of dissolved ionic compounds in water. See "brine."

"Sour gas" generally refers to natural gas containing acid gases such as hydrogen sulfide ($H_2S$) and carbon dioxide ($CO_2$). When the $H_2S$ and $CO_2$ have been removed from the natural gas feedstream, the gas is classified as "sweet." Generally, a gas is classified as sour when greater than about 4 ppm by volume of an acid gas is present, although in some contexts, gas up to 50 ppm by volume may be considered to be sweet. The term "sour gas" is applied to natural gases that include $H_2S$, because of the odor that is emitted even at low concentrations from an unsweetened gas. $H_2S$ is corrosive to most metals normally associated with gas pipelines so that processing and handling of sour gas may lead to premature failure of such systems.

"Sour gas stream" refers to a hydrocarbon fluid stream wherein the fluids are primarily in a gaseous phase, and contain at least 3 mol percent carbon dioxide and/or more than 4 ppm hydrogen sulfide.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

Overview

Formation history of rock samples has been typically determined by optical examination of microscopic thin-sections in order to surmise the history of the rock evolution. However, these analyses are limited by the information that may be obtained from microscopic or spectroscopic analyses, such as composition and grain distribution, among others. As noted above, isotope ratio measurement of rock samples may be used to determine the formation history of the rock. However, isotopic techniques that have been previous used have either used a bulk analysis, losing spatial information, or failed to appropriately correct for matrix effects, losing the accuracy needed for isotope ratio determination.

In exemplary embodiments of the present techniques, the isotope ratios of the mineral deposits within the grains in a rock sample are quantitatively analyzed by a secondary ion mass spectrometer, ion probe, or similar focused-ion-beam mass-spectrometer device (collectively referred to here as a "SIMS"). A multiple matrix correction in a SIMS analysis may provide sufficient accuracy and spatial resolution to determine the history of the sequence of temperature and chemical conditions of a rock sample.

However, the techniques described herein are not limited to rock samples and may be useful in forensic analysis, ice core analysis, sediment analysis, or for analysis in any other type of sample in which accurate isotope analysis on a microscopic scale would prove useful. The sample to be analyzed can include any material, including room temperature liquids which are solidified through use of a cooling stage, for example, by supporting the sample on a cryogenic platform during the analysis. For example, the techniques may be used to analyze fluid inclusions within rock samples or different ages of ice within glacial samples. The matrix corrected SIMS analysis provides highly-resolved spatial information, overcoming limitations such as small sample sizes and confusion due to analysis of multiple, spatially-overlapping phases.

In exploration for hydrocarbons, important reservoir properties that may be determined include, but are not limited to, the temperature and age of reservoir rock alteration, and identification of the process by which hydrocarbons have evolved (i.e., physical, thermal, and biological). Accurate determination of these properties can contribute, for example, to lowering the risk in the assessment of the hydrocarbon potential and quality of an exploration or exploitation opportunity. Therefore, selecting standards that are comparable to the matrix chemistry provides a useful correction to the values measured. The reservoir properties obtained from the analysis may be used to constrain the models used to calculate the evolution of hydrocarbons as they form over geologic time. The techniques may be used, for example, to measure core samples from a hydrocarbon field or reservoir, as shown in FIG. 1.

FIG. 1 is a schematic view 100 of a reservoir 102, in accordance with an exemplary embodiment of the present techniques. The reservoir 102, such as an oil or natural gas reservoir, can be a subsurface formation that may be accessed by drilling wells 104, 106, and 108 from the surface 110 through layers of overburden 112. The reservoir 102 may have one or more faults 114 dividing areas, for example regions 116 and 118, and which may either restrict or enhance the flow of hydrocarbons. The wells 104, 106, and 108 may be deviated, such as being directionally drilled to follow the reservoir 102. Further, the wells can be branched to increase the amount of hydrocarbon that may be drained from the reservoir, as shown for wells 104 and 108. The wells 104, 106, and 108, can have numerous areas with perforations 120 (indicated as dots next to the wells) to allow hydrocarbons to flow from the reservoir 102 into the wells 104, 106, and 108 for removal to the surface.

A core sample of the reservoir 102, the overburden 112, or the underburden 122, may be obtained from one of the wells 104, 106, or 108. The core sample may include different materials. As discussed above, an accurate spatially resolved analysis of these materials may provide an indication of the potential for the well, as discussed further with respect to FIG. 2.

Figure 2:
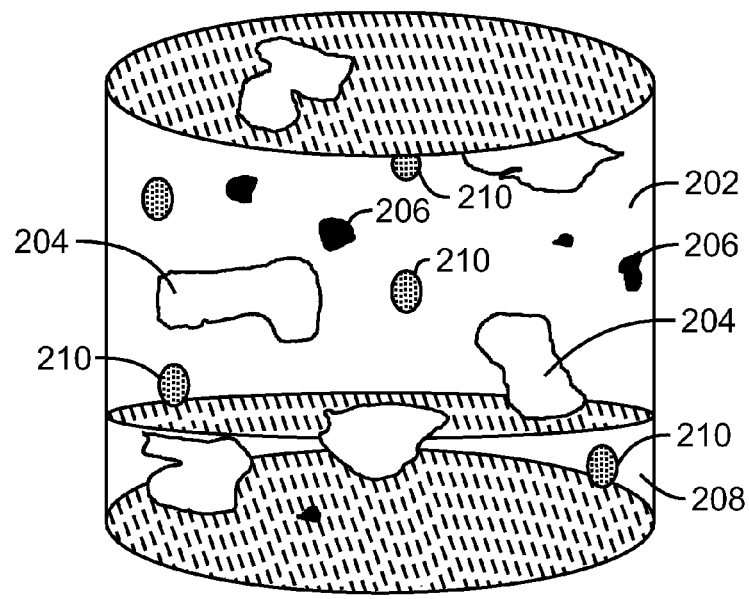
FIG. 2 is a drawing of a core sample from a well, in accordance with exemplary embodiments of the present techniques.

FIG. 2 is a drawing of a core sample 200 from a well, in accordance with exemplary embodiments of the present techniques. The core sample 200 may have a first matrix rock 202 that includes clastic grains, such as a sandstone, shale, siltstone, breccia, or other materials. The clastic grains may be silica, carbonates, quartz, feldspar, or any number of other materials that may be formed from weathering of other rocks. Embedded within the matrix rock 202 may be larger fragments of other rocks, such as gravel 204 (e.g., larger limestone fragments), igneous rock 206, or other materials. However, the core sample 200 may have no larger fragments 204 or 206, including only clastic grains. The core sample 200 may also have layers, such as a second matrix rock 208. Embedded within one or both of the matrix rocks 202 and 208 may be fluid inclusions 210, which may include, for example, hydrocarbons or water. By the time the core sample 200 is removed for analysis, gas inclusions may have escaped due to a decrease in pressure around the core sample. However, tight (low permeability) formations, such as shale, may trap such inclusions.

Accurate, spatially resolved isotope ratio analysis of the matrix rocks 202 and 208 may provide reservoir data that can be used in simulations, reservoir evaluation, and reservoir management. For example, analysis of grains forming a matrix rock 202 or 208 may provide a proxy for determining the permeability of the reservoir. Further, analysis results may provide estimates of how the samples are changing within wells, or between wells, which may be used to provide estimates of rock density for seismographic analysis. Any number of other geological measurements may benefit from the analysis. For example, a determination of grain formation history may be performed by the isotope ratio analysis, as discussed with respect to FIG. 3.

Figure 3:
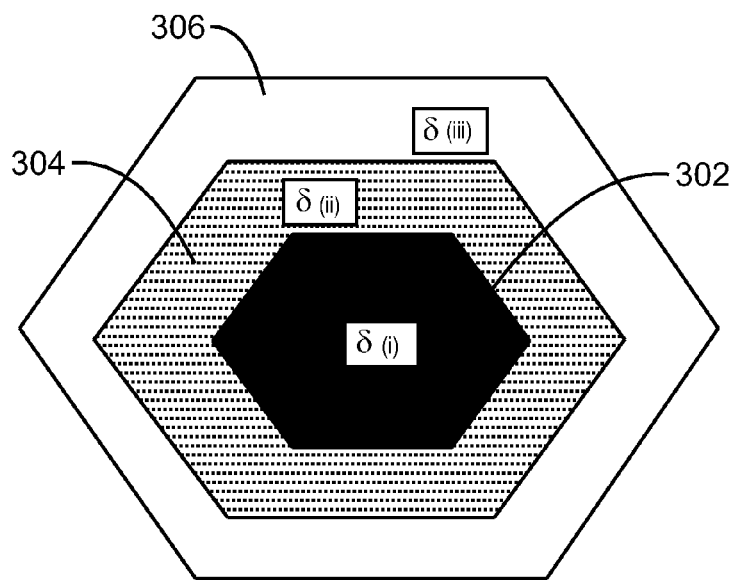
FIG. 3 is a drawing of a quartz grain, illustrating different layers having different formation histories, in accordance with an embodiment of the present technique.

FIG. 3 is a drawing of a quartz grain 300, illustrating different layers having different formation histories, in accordance with an embodiment of the present techniques. Previous techniques may not have had sufficient accuracy or spatial resolution to identify the multiple layers of a quartz grain. The core 302 of the quartz grain may have a first isotope ratio, e.g., $\delta^{18}O$. A middle layer 304 may have a different value for $\delta^{18}O$ as a result of forming at a different time or under different conditions of temperature and pressure. A third layer 306 may have yet another value for $\delta^{18}O$, due to formation under still different conditions of temperature or pressure. The layers 304 and 306 over the core 302 may be known as microquartz rims and may be correlated to porosity in a reservoir. Thus, the analysis of grains in core samples from current reservoirs may provide an indication of whether more wells should be drilled and in what areas. For example, the presence of microquartz rims may not be homogeneous across a reservoir and core samples from areas with microquartz rims may provide target areas for increased drilling.

The microquartz rims are not limited to the two layers 304 and 306 shown in FIG. 3, as any number of layers may form, depending on changes in the crystal growth environment over geologic history. Further, the quartz analysis discussed here is merely an example of one application of the technique. Any number of other rock types and isotopes may be analyzed to determine reservoir properties. For example, sulfur isotope ratios of organic materials in a reservoir may be used to indicate the history of the formation of the hydrocarbons in the reservoir, as discussed with respect to the example discussed with respect to FIGS. 13-15, below.

Instrument Systems and Interferences

Any number of instruments may be used in embodiments of the present techniques. One of these instruments is the secondary ion mass spectrometer or SIMS discussed with respect to FIG. 4. As used herein, SIMS is a generic term that encompasses all of the instruments that may be used, including atom probe, laser desorption mass spectrometry, and reactive vapor mass spectrometry, among others.

Figure 4:
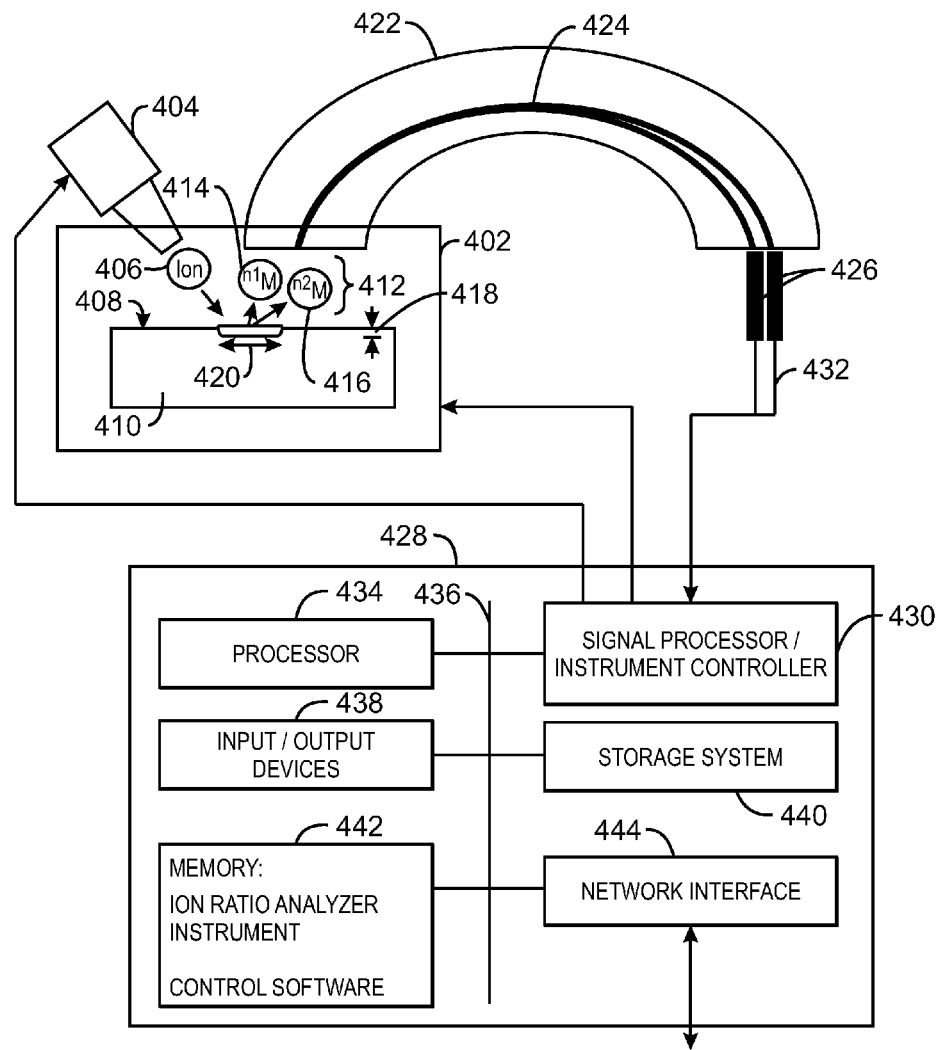
FIG. 4 is an example of a SIMS that may be used in exemplary embodiments of the present techniques.

FIG. 4 is an example of a SIMS 400 that may be used in exemplary embodiments of the present techniques. In the SIMS 400, a high vacuum chamber 402 may enclose the outlet of an ion generator 404 that fires an ion beam 406 at a surface 408 of a sample 410. The ion beam 406 strikes the surface 408, causing the ejection of secondary ions 412. The ion generator 404 may include any number of ion sources, such as duoplasmatrons, electron ionization sources, surface ionization sources, liquid metal ion sources, and the like. The ion source chosen may control the type of ion beam 406 generated. For example, ion beams 406 that may be generated in the present techniques may include ionized gases, such as $Ar^+$, $Xe^+$, $O^-$, $O_2^-$, or molecules, such as $SF_5^+$. Other ion beams 406 that may be used include metal ions, such as $Cs^1$. The ion source is not limited to ion beams 406, as other techniques may be used to generate ions in proximity to the surface. For example, a laser that is focused on or near the surface may create ions in a reactive atmosphere introduced into the vacuum chamber 402. Further, in embodiments that use an atom probe, the ion generator 404 may be the tip of a nearly atomically sharp probe, which has a hole for ion collection. The tip of the atom probe may generate secondary ions 412 by using an electrical pulse transmitted to the sample surface 408 from the tip to ionize the sample surface 408. The secondary ions 412 formed may then be collected through the hole.

SIMS is a counting technique that can measure an isotope ratio between a first isotope 414 and a second isotope 416 in the ejected secondary ions 412 and, thus, at the surface 408 from which said ions were extracted of the sample 410 The number of counts of each isotope 414 and 416 that is used to determine the isotope ratio may control the amount of material that may be removed from the surface of the sample. For some materials, the number of each secondary ion 412 that may be used to determine the isotope ratio may be greater than about $1 \times 10^6$, with a ratio of about 10 between the two ions. Thus, the spatial resolution, e.g., the depth 418 and spot size 420, may be determined by the amount of isotopes used to determine the ratio.

Further, the choice of the ions to be used in the ion beam 406 and, thus, the choice of ion generator 404 may influence the horizontal resolution of the technique. For example, a more tightly focused ion beam 406 may cover a smaller spot size 420. In this case, the depth 418 may be increased to obtain the same number of secondary ions 412 ejected from the surface, improving the lateral resolution. The choice of ions in the ion beam 406 may also be controlled by the chemistry of the atoms to be measured. For example, to create negative ions for the measurement of sulfur or carbon isotope ratios, $O_2$ or Cs may be used to form the ion beam 406.

In an exemplary embodiment, the depth 418 is about 10 nm and the spot size 420 is about 25 to 50 nm, although the technique is not limited to these values, as greater or lesser depths 418 and spot sizes 420 may be used. For example, an improvement in ionization efficiency, such as by selecting highly reactive ions for the ion beam 406, may allow for a smaller spot size 420. In this case, depths as small as about 1 nm may be possible. A laser could be used for post-collection ionization of the ejected material, further improving the ionization efficiency. For example, the ionization that may be achieved may be greater than about 1% of the ejected material using these techniques. However, any ionization may be used by increasing the sample size to compensate for lower levels of ionization, for example, 0.75%, 0.5%, 0.25%, or less.

The secondary ions 412 can be captured and transmitted through a mass analyzer 422, which generally sorts the ions by the ratio of mass-to-charge. Any number of mass analyzers 422 may be used in embodiments, including, for example, a magnetic analyzer, a quadrupole analyzer, or a time-of-flight (TOF) mass analyzer, among others. In the exemplary embodiment illustrated in FIG. 4, the SIMS 400 is a sector field mass spectrometer and, thus, a magnetic analyzer is used as the mass analyzer 422. In embodiments that use an atom probe to determine the isotope ratio of a sample surface 408, a TOF mass analyzer may be used. Ions that are not within a selected range of the mass-to-charge ratio of the target ions may be eliminated from the ion stream 424 by the mass analyzer 422, which may allow only the target isotopes 414 and 416 to reach a detector 426. In embodiments based on atom probes, the detector 426 may be time-gated to isolate the target isotopes 414 and 416 from the TOF analyzer.

The mass analyzer 422 and detector 426 may be subject to bias, which may result in an inaccurate measure of the number of each of the target isotopes 414 and 416 reaching the detector 426. The response of the instrument to measure a particular isotope ratio, termed instrumental mass fractionation or IMF, may affect the measured isotope ratios. The IMF can change, or drift, over time. In an exemplary embodiment, a series of accepted isotope ratio standards are used to develop a working standard calibration curve, as discussed further with respect to FIGS. 6-8, below. In an exemplary embodiment, the accepted isotope ratio standards are silver sulfide ($Ag_2S$) standards (such as IAEA-S-1, IAEA-S-2, and IAEA-S-3 available from the International Atomic Energy Agency (IAEA)), which may be used for calibrating the instrument for $\delta^{34}S$ analysis. In other embodiments, other standards can be used for other isotopes. For example, oxygen isotope ratio analyses may be calibrated using VSMOW2, SLAP2, GISP, or other standards available from the IAEA. The standards may be generally traceable to accepted values for isotope ratios. For example, the value for $\delta^{34}S$ for the $Ag_2S$ reference standards may be based on Vienna Canyon Diablo Troilite (VCDT), while the values for $\delta^{18}O$ may be based on Vienna Standard Mean Ocean Water (VSMOW), as discussed below.

It will be understood by one of ordinary skill in the art that generating the calibration curve requires at least two standards. After the working standard calibration curve is created, a working standard of the same chemical composition (e.g., chemical matrix) may be selected and run against the working standard calibration curve to determine the isotope ratio. This provides an operational standard to correct the instrument for IMF.

Any number of types of detectors 426 may be used in embodiments of the present techniques. For example, the detector 426 may include a Faraday cup, an electron multiplier, a microchannel plate detector, a resistive-anode encoder, a channeltron, a charge coupled device (CCD), or even an optical detector, such as a fluorescent screen coupled with a camera. The selected ions from the ion stream 426 may be individually detected by the detector 426, and counted by electronics in an instrument control system 428.

The instrument control system 428 may have a number of units to facilitate the measurement of isotope ratios. A signal processor/instrument controller 430 may process the signal 432 from the detector 426, converting the signal from an analog signal to a digital signal. Further, the signal processor/instrument controller 430 may have control circuits that adjust the ion generator 404, for example, to focus the ion beam 406, or to move the sample 410 in the vacuum chamber 402, among others. The signal processor/instrument controller 430 may communicate with other units in the instrument control system 428 over a bus 436.

The instrument control system 428 may have a processor 434 coupled to the bus 436 to control the signal processor/instrument controller 430. In addition, the instrument control system 428 may include input/output devices 438, such as displays, mice, general keyboards, instrument specific keyboards, and printers, among others. The input/output devices 438 may be used to obtain user input for controlling the process and provide an output of the results. The instrument control system 428 may also have various types of non-transitory, computer readable media, including a storage system 440 and memory 442. The storage system 440 may be used for long term, non-volatile storage of operational programs and data, as well as programs for implementing the methods of the current techniques, for example, as discussed with respect to FIG. 6. The memory 442 may include random access memory (RAM) or read only memory (ROM), which may store operational copies of the instrument control software, as well as the code used to implement an isotope ratio analysis. A network interface 444 may couple the bus 436 of the instrument control system 428 to an external network.

Figure 5:
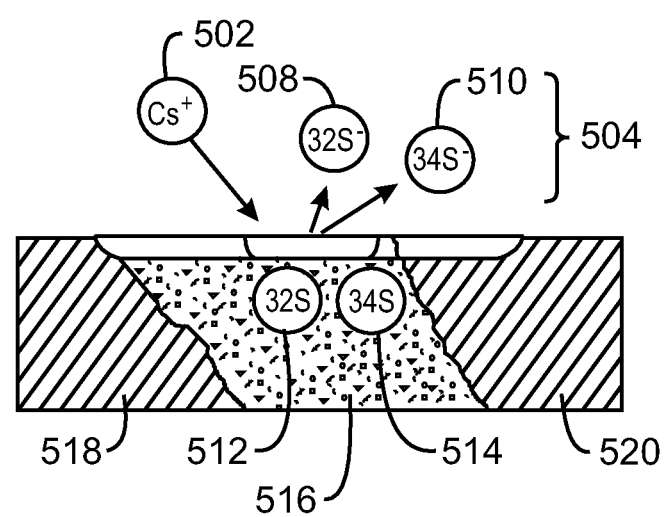
FIG. 5 is a schematic illustration of a sample that is being analyzed for a ratio of $^{34}S$ to $^{32}S$ ($\delta^{34}S$), in accordance with an exemplary embodiment of the present techniques.

FIG. 5 is a schematic illustration of a sample 500 that is being analyzed for a ratio $^{34}S/^{32}S$ ($\delta^{34}S$), in accordance with an exemplary embodiment of the present techniques. In this exemplary embodiment, the sample 500 is being bombarded with $Cs^+$ ions 502. As a result, material 504 may be ejected from the surface 506 of the sample 500. The ejected material 504 includes numerous different charged and uncharged species, such as $^{32}S^-$ ions 508 and $^{34}S^-$ ions 510.

However, the ratio of the ions 508 and 510 in the ejected material 504 may not match the ratio of the $^{32}S$ isotope 512 to the $^{34}S$ isotope 514 in the sample 500. As previously mentioned, this can be due to minor chemical differences between the isotopes 512 and 514, which change their chemical interaction with the sample matrix 516 and, thus, change the rate at which they may be elected from the sample surface 506. Accordingly, the ratio of $^{32}S^-$ ions 508 to the $^{34}S^-$ ions 510 from a second sample matrix 518 may be different, even if the ratio of the $^{32}S$ isotope 512 to the $^{34}S$ isotope 514 was the same. Thus, as the analysis proceeds from the first matrix 516 to a second matrix 518, or to a third matrix 520, the results of the analysis will be distorted by the composition of the matrix 516, 518, and 520. In exemplary embodiments of the present techniques, standard matrices are identified that may bracket a range of sample matrices. For example, the standard matrices may have atomic compositions, molecular components, and other characteristics in common with the sample matrices. The standard matrices may then be used to create a calibrated matrix correction curve. Using the calibrated matrix correction curve, the results may be corrected for matrix effects. The procedure to develop the calibrated matrix correction curve is discussed in further detail with respect to FIGS. 6-12, below.

Process for Generating Matrix Corrected Calibration Curves for SIMS

Figure 6:
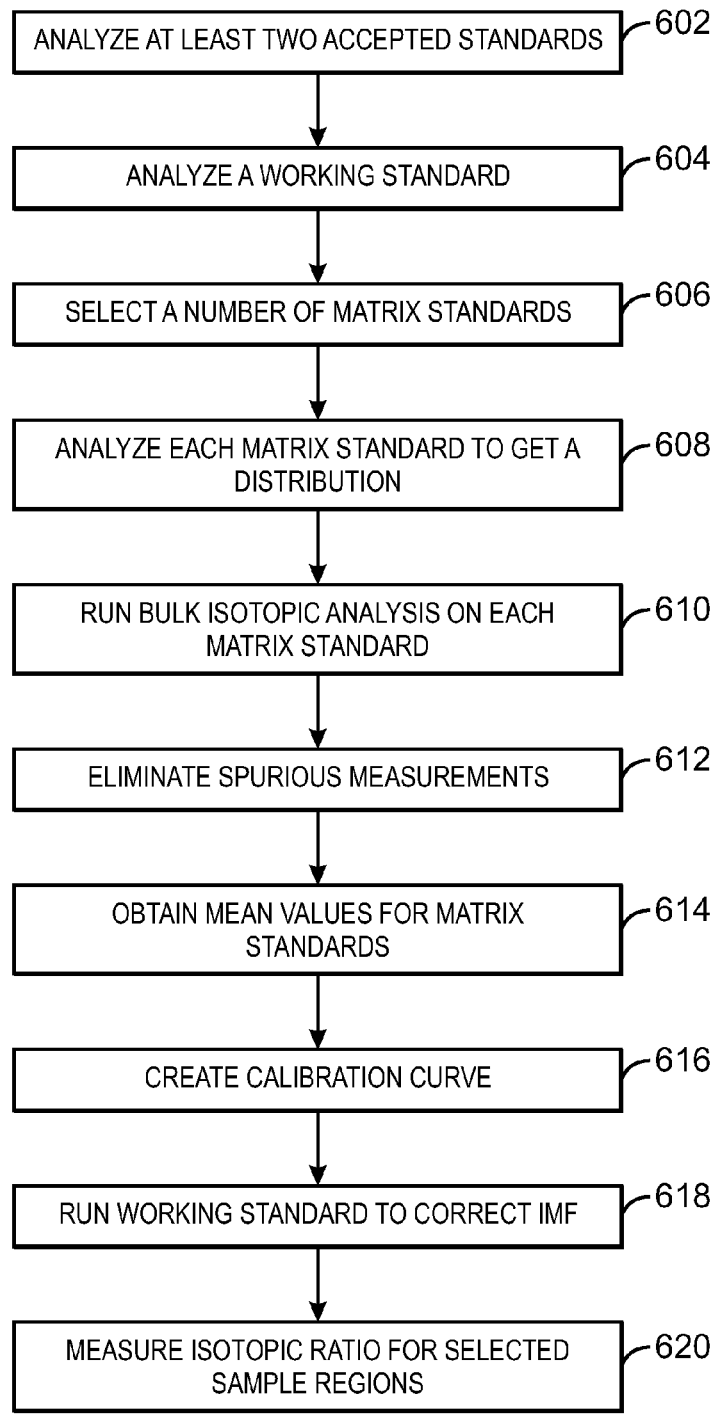
FIG. 6 is a process flow diagram of a method for correcting SIMS measurements for matrix effects, in accordance with exemplary embodiments of the present techniques.

FIG. 6 is a process flow diagram of a method 600 for correcting SIMS measurements for matrix effects, in accordance with exemplary embodiments of the present techniques. The method 600 begins at block 602 with the analysis of at least two accepted standards. More standards would provide more accuracy, but two will provide an initial calibration curve that may be used to calibrate a working standard. As described previously, the accepted standards may be international isotope standards that are commercially available. However, the accepted standards are not limited to international isotope standards, and may be any standards for which the analyst believes that reasonably accurate data may be obtained for both the bulk and SIMS measurements of the target isotopes.

At block 604, a working standard is selected for correcting for IMF. The working standard may be a lower cost material that may be used in greater quantities (for example, daily measurements) than the generally more expensive accepted standards. The values for the ratios of the isotope ratios are measured by both the bulk isotope measurements and by SIMS isotope measurements. The values are then plotted along the calibration curve to determine the isotope ratio measurement for IMF corrections.

At block 606, a number of matrix standards are selected to develop a matrix corrected calibration curve. In exemplary embodiments, matrix standards that produce meaningful corrections are selected, for example, matrix standards with known geologic histories. In lieu of actual rock or mineral standards, standards with similar chemical composition and bonding may be selected as surrogates for natural standards.

The matrix standards may be identified by taking materials that have a close chemical composition to the target matrix, then running analytical tests to identify the most similar matrices. The analytical tests may include microscopic phase analyses using such techniques as x-ray diffraction, x-ray photoelectron spectroscopy (XPS), Auger spectroctrometry, IR microprobe, and the like.

In an exemplary embodiment, bitumen was identified as a target material for a $\delta^{34}S$ analysis, as discussed with respect to the example below. It was noted that petroleum coke had a similar atomic composition to the bitumen. Further, bulk isotope ratio analysis of the petroleum coke showed a similar range of values for $\delta^{34}S$, and a similar range of bonding environments. However, the techniques are not limited to petroleum coke, as any number of materials may be used as a matrix standard, depending on the target isotopes and matrix. For example, natural or artificial hydroxylapatite samples may be used as matrix standards for $\delta^{18}O$ analysis in bone samples, potentially allowing the use of the techniques described herein in forensic analysis. Other potential applications are discussed below.

Materials with substantial heterogeneity may not make good matrix standards, as the variation across the sample may be problematic. However, this effect may be at least partially corrected by eliminating spurious measurements from the matrix standards. At block 608, each of the matrix standards can be analyzed by SIMS to obtain a distribution of values across the surface. A bulk isotope ratio analysis can then be run for each matrix standard at block 610, for example, using techniques such as standard plasma mass spectrometry or, isotope ratio mass spectrometry, among others. Plotting the values from the SIMS and bulk isotope ratios against each other can be used to determine the isotope variation across the matrix standard.

Since a narrower distribution may make the analysis more accurate, spurious measurements may be eliminated at block 612. This may be performed by any number of qualitative or quantitative techniques, including, for example, statistical tests to determine outliers, mapping of the isotope ratios across the surface to select the most representative matrices in the matrix standard, weighing the values prior to averaging the values, and the like. At block 614, the remaining values are averaged to obtain a mean value for each of the matrix standards. At block 616, a matrix specific calibration curve may be created by using a least-squares fit to create a line through the mean values for each of the matrix standards. As discussed further below, the matrix corrected calibration curve does not have to he a straight line, as other functions may be useful.

The calibrated working standard and the matrix corrected calibration curve can then be used to analyze isotope ratios in target samples. At block 618, the working standard can be run to correct for IMF. This can be performed as often as practical, as determined by the instrument drift of the SIMS. For example, the working standard can be used to correct for IMF after each sample, after a certain number of samples, once per day, once per each continuous period of instrument operations, or any other suitable period. At block 620, the isotope ratio is measured for the target sample. A number of values may be measured for a particular matrix in the sample and averaged. As for the matrix standards, any spurious measurements (such as isotope values from other matrices in the sample) may be identified and eliminated. The remaining values play be averaged, and the average compared to the matrix corrected calibration curve to determine the isotope ratio for the sample. The steps above may be more clearly understood by graphs of the relevant values, as shown in FIGS. 7-12.

Figure 7:
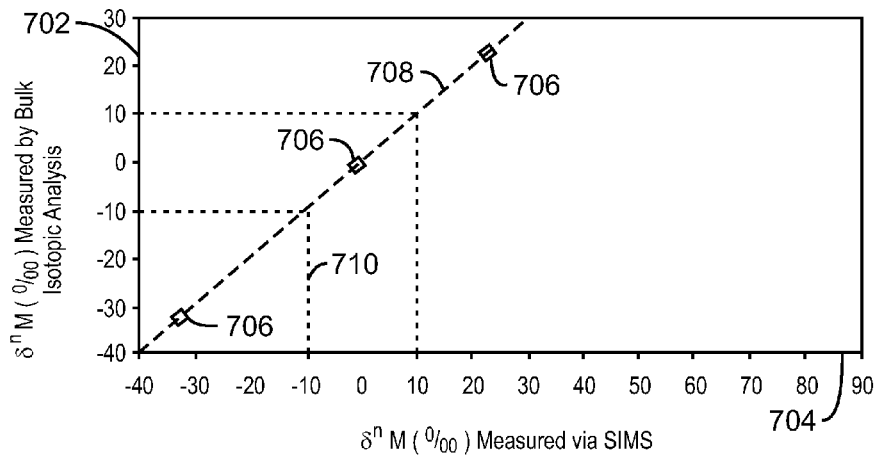
FIG. 7 is a graph illustrating the generation of the working standard, in accordance with an embodiment of the present techniques.

FIG. 7 is a graph illustrating the generation of the working standard, in accordance with an embodiment of the present techniques. The x-axis 704 for this graph, and the succeeding graphs, is the value of $\delta''M$ in parts per thousand (‰) as measured by SIMS. The y-axis 706 for this graph, and the succeeding graphs, is the value of $\delta''M$ in parts per thousand (‰) as measured by a bulk isotope analysis. The value of $\delta''M$ may be expressed as the formula shown in Eqn. 2.

$$\delta^n M = \left( \frac{\left(\frac{n1M}{n2M}\right)_{sample}}{\left(\frac{n1M}{n2M}\right)_{standard}} - 1 \right) * 1000 \, o/oo \qquad \text{Eqn. 2}$$

Thus, the values for $\delta''M$ are reported as a shift from a standard isotope reference (standard in Eqn. 2) which has an accepted value of 0‰ for the measurement. For example, sulfur isotope ratio analyses, $\delta''M$, are reported as a shift from the ratio of $^{34}S$ to $^{32}S$ in a sample of Vienna Canyon Diablo Troilite or CDT. Similarly, the values for $\delta^{18}O$ are reported as a shift from the ratios of $^{18}O$ to $^{16}O$ in Vienna Standard Mean Ocean Water (VSMOW).

As discussed with respect to block 602 of FIG. 6, a number of accepted standards 706 may be analyzed and used to generate a calibration curve 708. The calibration curve may be used for the analysis of working standards. In some situations, the calibration curve 708 may have a slope of one, as indicated by the dashed lines 710. This may indicate that the bulk isotope ratio is providing the same results as the SIMS analysis, showing that matrix effects are minimal for the accepted standards. The techniques are not limited to accepted standards that have a slope of one, as other accepted standards may be selected that have matrix effects, i.e., that generate a calibration curve 708 with a slope that is not unity.

Figure 8:
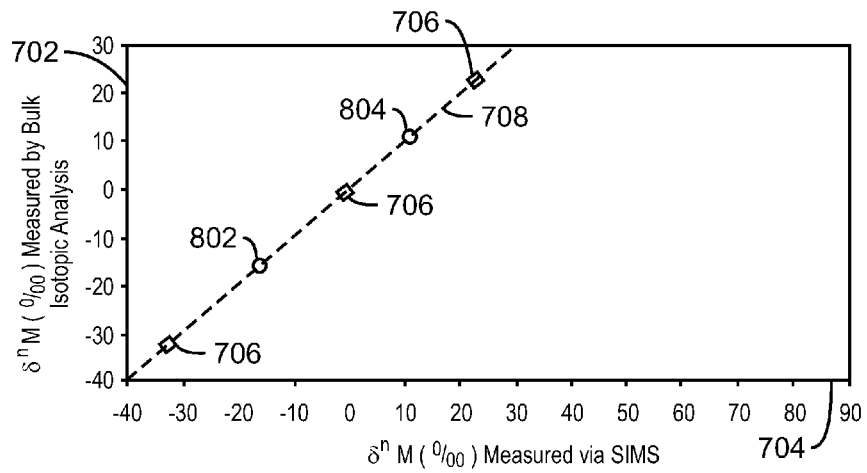
FIG. 8 is a graph plotting working standards on the calibration curve generated in FIG. 7, in accordance with an exemplary embodiment of the present technique.

FIG. 8 is a graph 800 plotting working standards 802 and 804 (discussed with respect to block 604) along the calibration curve generated in FIG. 7, in accordance with an exemplary embodiment of the present technique. The axes 702 and 704 are the same as described in FIG. 7. Although one working standard 802 may typically be used, more working standard, such as working standard 804 may provide corrections of IMF in other regions. This may help to compensate for non-linear changes in IMF.

Figure 9:
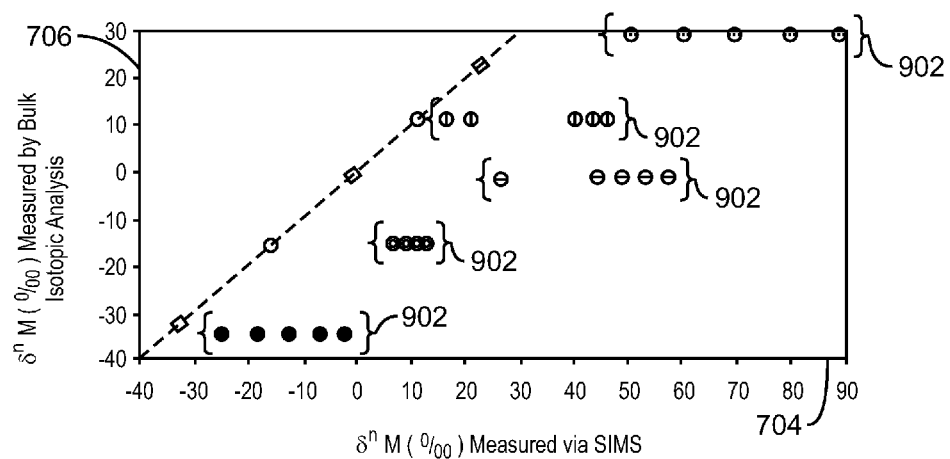
FIG. 9 is a graph showing the plotting of matrix standards on the graph of FIG. 7, in accordance with an exemplary embodiment of the present techniques.

FIG. 9 is a graph 900 showing the plotting of matrix standards 902 on the graph of FIG. 7, in accordance with an exemplary embodiment of the present techniques. The selection and analysis of the matrix standards is discussed with respect to block 606-610 in FIG. 6. As can be seen in the graph 900, each of the matrix standards 902 is uniform with respect to the bulk measurement of isotope ratios, as shown on the y-axis 706. Such uniformity may be expected from a preparation procedure that homogenizes the samples, e.g., by dissolution in acid. However, the matrix standards 902 show a substantial variation with respect in the SIMS measurement, as shown on the x-axis 704. This may be expected from a technique that can measurement variations across a sample matrix with a microscopic resolution.

Figure 10:
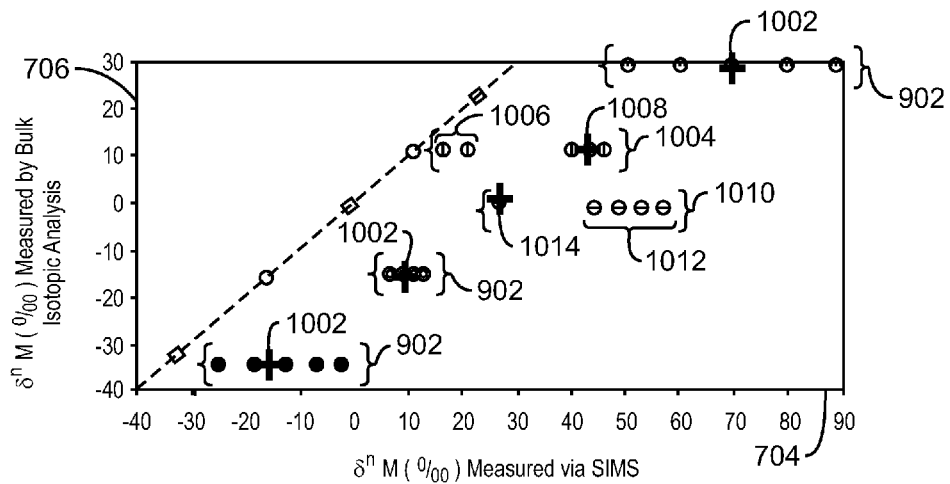
FIG. 10 is a graph showing the elimination of spurious measurements and the calculation of an average value for each of the matrix standards, in accordance with an exemplary embodiment of the present technique.

FIG. 10 is a graph 1000 showing the elimination of spurious measurements and the calculation of an average value for each of the matrix standards, in accordance with an exemplary embodiment of the present technique. This illustrates the techniques discussed with respect to blocks 612 and 614 of FIG. 6. As can be seen in this graph 1000, two types of variation may be seen for sets of the matrix standards. In the first type of variation, a first set of matrix standards 902 may have a uniform variation or distribution, which may indicate a substantially homogeneous sample. For these matrix standards 902, an average 1002 may be calculated using all of the sample values.

However, other matrix standards, such as the second set of matrix standards 1004, may have some values, such as group 1006, that are offset from other values. The offset for group 1006 may indicate that more than one matrix has been analyzed in the standard. The statistical techniques described with respect to block 612 above may be used to eliminate the spurious group 1006, allowing an average 1008 to be taken of the remaining measurements. A similar circumstance may be noted for other matrix standards 1010, in which a group 1012 of measurements is offset from the other measurements. After elimination of the spurious group 1012, an average 1014 may be calculated for the remaining measurements. Once the averages are calculated, a matrix corrected calibration curve may be generated.

Figure 11:
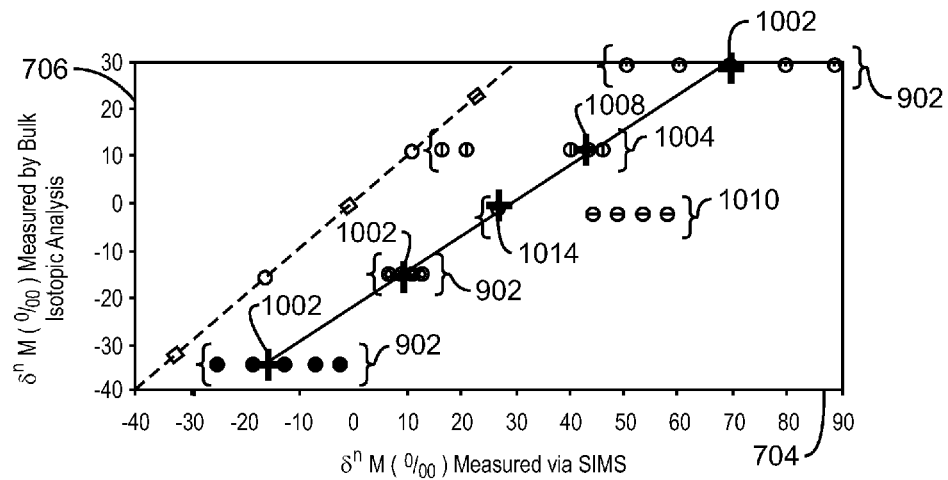
FIG. 11 is graph illustrating the generation of the matrix corrected calibration curve, in accordance with exemplary embodiments of the present techniques.

FIG. 11 is graph 1100 illustrating the generation of the matrix corrected calibration curve 1102, in accordance with exemplary embodiments of the present techniques. The matrix corrected calibration curve 1102 can be generated by performing a least squares regression through the mean values 1002, 1008, and 1014 of the matrix standards 902, 1004, and 1010. Although the matrix corrected calibration curve 1102 is shown as a straight line in the graph 1100, more complex functions may be used, depending on the linearity of the matrix correction. In embodiments, the matrix corrected calibration curve 1102 could be based on an exponential function, an inverse function, a quadratic function, or any number of other functions. Once the matrix corrected calibration curve 1102 is generated, it may be applied to the analysis of isotope ratios for samples.

Figure 12:
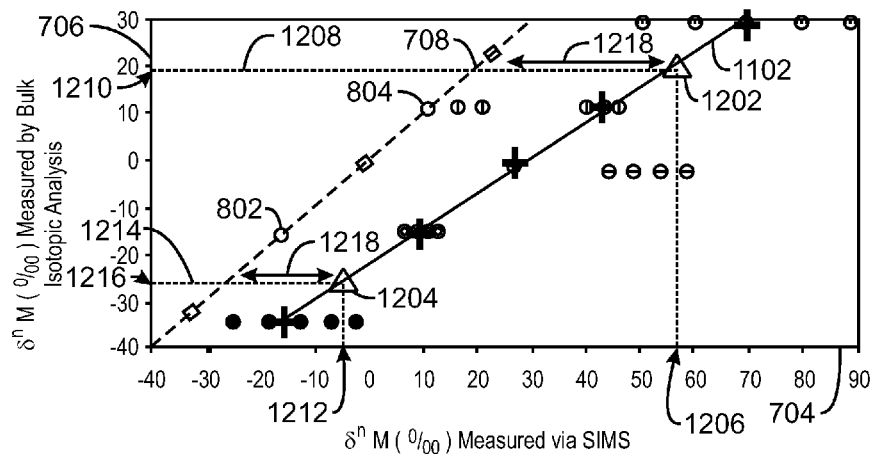
FIG. 12 is a graph showing the use of the matrix corrected calibration curve for the isotope analysis of samples, in accordance with exemplary embodiments of the present techniques.

FIG. 12 is a graph 1200 showing the use of the matrix corrected calibration curve 1102 for the isotope analysis of samples, in accordance with exemplary embodiments of the present techniques. To begin, one or both of the working standards 802 and 804 may be run to correct the SIMS for IMF. The unknown samples may then be analyzed and averaged. The mean values 1202 and 1204 from the isotope ratios as measured by the SIMS can then be plotted along the matrix corrected calibration curve 1102. The matrix corrected values may then be determined by reading the value from the y-axis 706. For example, if the SIMS measurement of unknown sample 1 1202 gave a value 1206 for δ"M of about 57‰, a line 1208 could be projected from the matrix corrected calibration curve 1102 to the y-axis 706. A value 1210 of δ"M of around 19‰ could then be estimated for the isotope ratio of unknown sample 1 1202. Similarly, if unknown sample 2 1204 has a SIMS measured value 1212 for the isotope ratio of −5‰, a line 1214 projected from the matrix corrected calibration curve 1102 to the y-axis 706 can be used to determine that unknown sample 2 1204 has a value 1216 for the isotope ratio of about −25. It should be noted that the separation 1218 between the matrix corrected calibration curve 1102 and the calibration curve 708 is the matrix effect and shows the distortion that the matrix causes in the measurement. Further, the separation 1218 varies with δ"M, making a single point correction (e.g., as currently performed in the art) to be inaccurate.

Example: Correction Factors for Sulfur Isotopes in Bitumen

The techniques described above were tested for the determination of $\delta^{34}S$ in a bitumen sample. Through the application of the techniques, the sulfur ratio may be quantified at selected areas within the sample. The value for $\delta^{34}S$ may be represented by the formula shown in Eqn. 3.

$$\delta^n M \equiv \delta^{34}S = \left( \frac{\left(\frac{^{34}S}{^{32}S}\right)_{sample}}{\left(\frac{^{34}S}{^{32}S}\right)_{CDT}} - 1 \right) * 1000 \, o/oo \qquad \text{Eqn. 3}$$

In Eqn. 3, CDT refers to the isotope standard, Vienna Canyon Diablo Troilite. Through precise measurements of the standards and unknowns, as discussed above, this ratio may be determined. Suitable corrections can also be made for the IMF and matrix effects.

Figure 13:
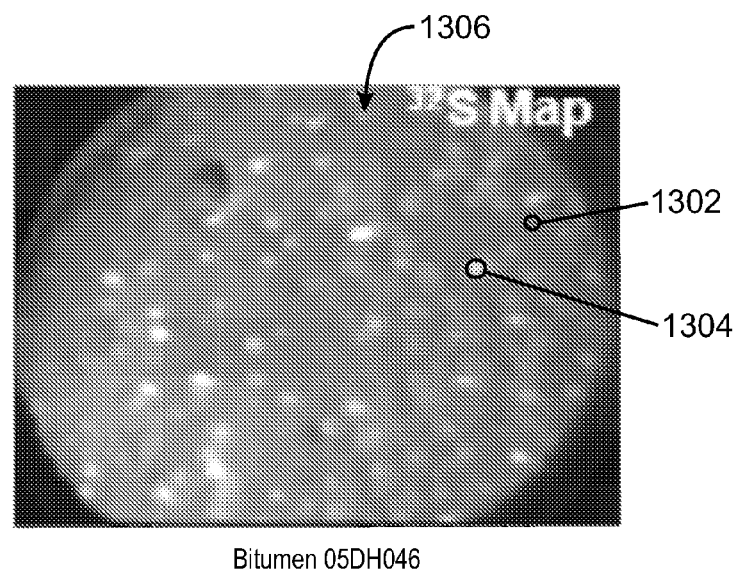
FIG. 13 illustrates a map of the concentration of $^{32}S$ at a surface of a sample of bitumen from a hydrocarbon deposit, in accordance with an exemplary embodiment of the present techniques.

FIG. 13 illustrates a map 1300 of the concentration of $^{32}S$ at a surface of a sample of bitumen from a hydrocarbon deposit, in accordance with an exemplary embodiment of the present techniques. As can be seen in the map 1300, there may be lower concentration zones 1302 and higher concentration zones 1304 (indicated by the lightness of the image), among others. Further, even a single concentration zone 1302 or 1304 may have substantial heterogeneity for the isotope ratio. Conventional analysis by mass spectrometry makes the assumption that the material is homogeneous, which would result in averaging both the sulfur concentrations and isotope ratios of the two components. The previously discussed techniques for microscale analysis, such as micromilling, microdrilling, or laser ablation may not have sufficiently fine resolution to analyze a particular location 1306 in the map 1300. Further, current techniques for isotope analysis do not use separate corrections for IMF and matrix effects, which may lead to inaccurate determination of the ratios for different areas of the sample.

Petroleum coke (termed "coke") may have the same general concentration range for carbon and sulfur, and a similar range of chemical matrices as the bitumen. Accordingly, coke samples may be used as matrix standards for generating a matrix corrected calibration curve for the microscale analysis of bitumen samples.

Figure 14:
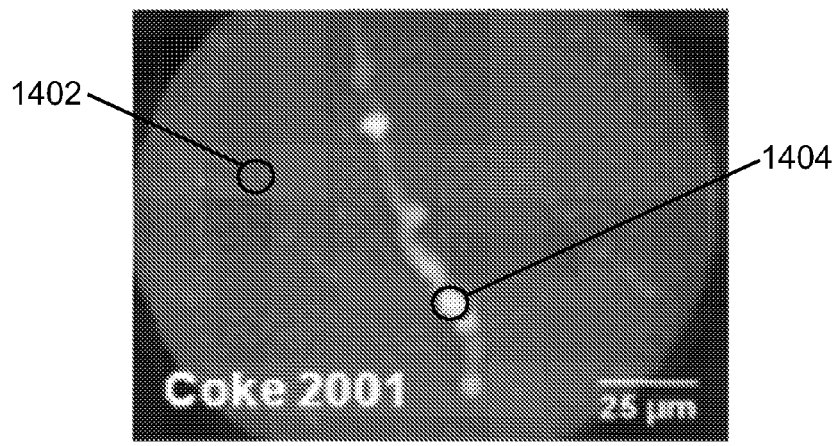
FIG. 14 illustrates a map of the concentration of $^{32}S$ at a surface of a sample of coke, in accordance with an exemplary embodiment of the present techniques.

FIG. 14 illustrates a map 1400 of the concentration of $^{32}S$ at a surface of a sample of coke, in accordance with an exemplary embodiment of the present techniques. As for FIG. 13, the map 1400 illustrates that lower 1404 and higher 1402 concentrations of sulfur may exist across the surface of the coke, for example, the higher concentration region 1404 may represent a region having a high concentration of sulfide. Further, the sulfide in the higher concentration region 1404 has a significantly different $\delta^{34}S$ from the surrounding coke, e.g., a $\delta^{34}S$ of about −70‰ versus a $\delta^{34}S$ of about 30‰ for lower concentration region 1402. Conventional mass spectrometry would average the isotope ratios of these two components, potentially resulting in an unacceptable uncertainty. The large negative value for the sulfide in the higher concentration region 1404 indicates an isotope fractionation that would be missed in a conventional analysis. Such fractionations in the petroleum reservoir are potentially important in revealing details on the geologic history. The map 1400 also illustrates that the matrix of a coke may be more uniform than the matrix of a bitumen sample, allowing different cokes to be chosen for providing a range of matrix standards for the analyses of the bitumen. This is illustrated for this example by the graph in FIG. 15.

Figure 15:
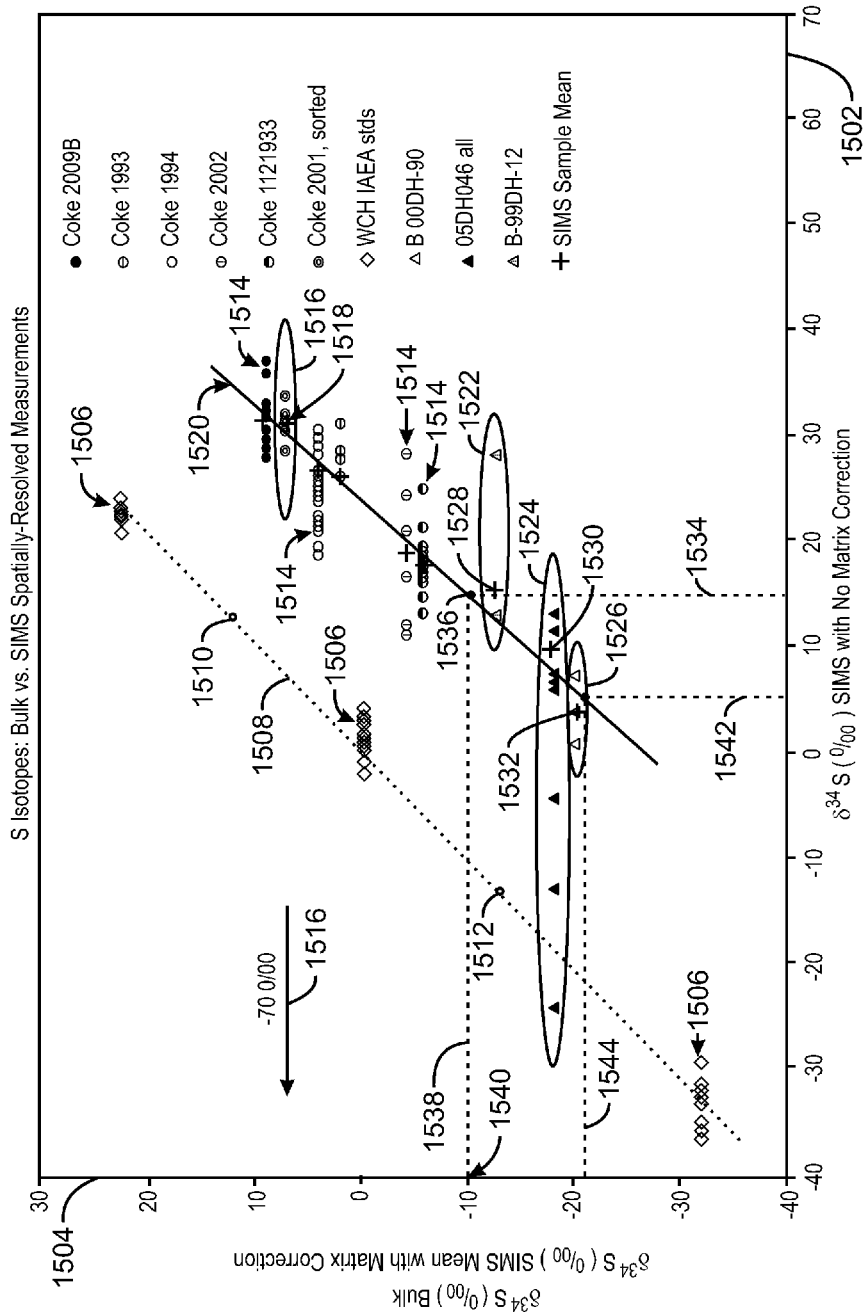
FIG. 15 is a graph illustrating the application of the techniques described herein to analyze the sulfur isotope ratio in bitumen samples, in accordance with an exemplary embodiment of the present techniques.

FIG. 15 is a graph 1500 illustrating the application of the techniques described herein to analyze the sulfur isotope ratio in bitumen samples, in accordance with an exemplary embodiment of the present techniques. The protocol illustrated in FIGS. 6-12 was used to obtain a matrix corrected calibration curve. In the graph 1500, the x-axis 1502 represents the $\delta^{34}S$ values obtained from a SIMS analysis without a matrix correction. The y-axis 1504 represents both the $\delta^{34}S$ obtained from a bulk isotope analysis and the matrix corrected value of $\delta^{34}S$ for the SIMS measured value.

As illustrated in the graph, a number of accepted standards 1506 (in this example, IAEA standard $Ag_2S$ references) were run by both SIMS and bulk isotope analysis. A mean was taken of each group of accepted standards 1506, and used to generate a calibration curve 1508. A working standard 1510 was run and plotted against the calibration curve 1508 to provide a standard for regular IMF correction. As noted above, a second working standard 1512 may also be used. A series of coke samples was selected as matrix standards. Most of the matrix standards selected had substantially consistent values for $\delta^{34}S$ measured by SIMS, e.g., as seen for matrix standards 1514. However, a few of the matrix standards showed significant variation across a surface. For example, the matrix standard "Coke 2001" 1516 had values for $\delta^{34}S$ measured by the SIMS both in the range of $\delta^{34}S \approx +30‰$ and $\delta^{34}S \approx -70‰$, as discussed with respect to FIG. 14. The values of $\delta^{34}S$ in the range of –70‰ were identified via ion imaging as arising from secondary phases and were excluded from the analysis prior to the calculation of a mean 1518 for the matrix standard 1516. Once the spurious measurements were eliminated, mean values were calculated for each of the remaining matrix standards 1514. A linear least squares line was then fitted to the mean values to generate a matrix corrected calibration curve 1520.

The matrix corrected calibration curve 1520 was then utilized to obtain a high-precision isotope ratio. This was done by running the working standard 1510 or 1512 and corrected the SIMS for IMF. After correcting the SIMS for IMF, isotope analyses for each of the bitumen samples 1522, 1524, and 1526 were run by both SIMS and bulk techniques. The SIMS measurements for bitumen samples 1522 and 1524 showed substantial variation, so spurious measurements were eliminated prior to calculated a mean value 1528, 1530, and 1532 for each sample.

The mean values 1528, 1530, and 1532 were then used to determine the matrix corrected value for the SIMS measurement. For example, for bitumen sample 1522, the value of $\delta^{34}S$ for the SIMS mean 1528 may be read along the x-axis 1502 as about +16‰, as indicated by line 1534. This value may be projected onto a point 1536 along the matrix corrected calibration curve 1520. From this point 1536, a horizontal line 1538 may be projected to the y-axis 1504 were a matrix corrected value for $\delta^{34}S$ of about –10‰ may be read. By comparison, the bulk analysis of sample 1522 resulted in a $\delta^{34}S$ value 1540 of about –12‰.

The same steps may be used to determine the matrix corrected values for $\delta^{34}S$ for the remaining samples, 1524 and 1526. For example, projecting the mean 1532 for sample 1526 onto the x-axis 1502, as indicated by line 1542, provides a SIMS measurement value for $\delta^{34}S$ of about +3‰. Projecting this value onto the matrix corrected calibration curve, then horizontally to the y-axis 1504, as indicated by line 1544, results in a matrix corrected value for $\delta^{34}S$ of about –22‰. By comparison, the bulk isotope measurements for sample 1526 provided a value for $\delta^{34}S$ of about –20‰. Comparing the variation of the bulk samples to the matrix corrected value for the SIMS illustrated the accuracy for microscale analysis that may be gained by the techniques disclosed herein.

For example, an organic sample was tested and yielded a raw SIMS value of $\delta^{34}S = +30‰$. Using standard analysis techniques, a single standard was used to correct for both IMF and matrix effects. The resulting corrected value spanned a wide range, $-2 \leq \delta^{34}S \leq +15‰$, providing an unacceptable outcome to those skilled in the art. In contrast, the use of a matrix corrected calibration curve resulted in a value for $\delta^{34}S = +4 \pm 2‰$, which is an acceptable level of accuracy for reservoir rock analysis to those skilled in the art.

Other Applications

The techniques described herein discuss the use of spatially resolved measurements of isotope ratios via a secondary ion mass spectrometer, ion probe, or similar focused-ion-beam mass-spectrometer device or any device capable of measuring isotope ratios by atom counting such as an atom probe (collectively referred to here as a "SIMS"). The techniques may be useful for application in the areas of petroleum exploration, development, and production. Further, the techniques may be used for any analysis for which a complex matrix may distort the ratio of isotopes removed from a surface.

The spatially resolved measurements greatly improve the utility of such isotope ratio measurements over conventional methods that utilize larger sample sizes, for application in the areas of petroleum exploration, development, and production by permitting such measurements to be performed on individual, targeted phases of interest having microscopic dimensions, with high sensitivity and precision. This spatially resolved advantage minimizes the impact of spatially overlapping phases contributing to mixed information from individual analyses. Sub-percent to sub-permil precisions are achievable, depending upon operational variables such as analytical volume, concentration of species of interest, and data collection time.

In addition to the applications discussed above, the techniques may be used in any number of other applications. For example, the techniques may be used for the analysis of clastic reservoir quality. Clastic reservoir quality can be affected by natural grain coatings at both geological (e.g., quartz cement growth retardation/inhibition) and production (e.g., artificial diagenesis induced by thermally based oil recovery) timescales. The capability to determine the continuity and detailed isotope composition of such grain coatings would improve our understanding of their formation conditions.

Further, the techniques may be used to determining the origins of carbon in mineral cements, which may helps in understanding the diagenetic evolution of carbonate sediments during burial. For example, the ratio of $^{13}C$ to $^{12}C$ can discriminate between marine and non-marine origins, breakdown of organic matter, and bacterial methanogenesis.

The techniques may also be used to determining the temperature of precipitation of a mineral (carbonate, silicate, quartz overgrowths), by analyzing for the ratio of $^{18}O$ to $^{16}O$. Measuring the ratio of $^{34}S/^{32}S$ in sulfates, pyrite, and bitumen, may allow for differentiating between sulfur derived from sulphate reducing bacteria versus thermal maturation of organic matter in the deep subsurface.

The techniques described herein are not limited to determining ratios of isotopes, but may also be used for determining amounts of stable isotopes (such as C, N, O, S, Sr, Cl, Fe, Si) with high spatial resolution. The analyses may help to determine the geological histories for any number of materials, such as determining the source input, depositional settings, and thermal diagenesis/catagenesis for kerogen. The precursors, processes of formation, source of incorporated S, and thermal diagenesis/catagenesis for solid bitumen may be determined. The source macerals, and thermal diagenesis/catagenesis for coals may be determined. A high-resolution chemostratigraphic measurement of layers may be made to determine stratigraphic correlations, or paleoclimates. In addition, the reservoir connectivity of a hydrocarbon reservoir may be determined by an isotope correlation of latest forming cements.

techniques is not intended to be limited to the particular embodiments disclosed herein. Indeed, the present techniques include all alternatives, modifications, and equivalents falling within the true spirit and scope of the appended claims.

TABLE 1

Example of Carbon Isotope Ratio Analysis

| Total Sputter Time (sec) | $^{12}$C Tot Counts | $^{13}$C Tot Counts | $^{12}$C count error | $^{13}$C count error | $^{13}$C/$^{12}$C Precision (per mil) | Total C Atoms Sputtered | (100% Efficiency) Volume Sputtered ($\mu m^3$) | (0.001% Efficiency) Volume Sputtered ($\mu m^3$) |
|---|---|---|---|---|---|---|---|---|
| 10 | $1.00 \times 10^{+07}$ | $1.01 \times 10^{+06}$ | 0.316 | 0.995 | 1.044 | $1.10 \times 10^{+07}$ | $8.3 \times 10^{-06}$ | $8.3 \times 10^{-1}$ |

The techniques may be useful in geomicrobiology to determine biogenic mineral deposition and microfossils. In mineralogy/petrography, the techniques may be useful to determine paragenetic (carbonate and clastic) sequences, hydrothermal alteration, cementation, or clastic grain provenance.

The techniques may be used to determine organic/clay interactions, for example, to identify source rock deposition. The techniques may provide critical information to improve enhanced oil recovery, as well as improved reservoir characterization by secondary porosity processes, porosity and permeability alteration by fines or organics, and cementation processes. The SIMS techniques may also be used to determine organic mineralization (e.g., U, Fe, Mo) in order to differentiate the thermal maturity of a kerogen.

Extension of SIMS Method to Higher Spatial Resolution

Extension of the method to achieve even higher spatial resolution than commonly practiced may be achieved. The process limits that can be theoretically achieved may be estimated. As described above, the SIMS technique may utilize a volume of about $10^2$ $\mu m^3$ for isotope analysis. Using carbon isotopes as an example, it can be demonstrated that much smaller volumes should be possible. Details of the calculation are shown in Table 1 below. Graphite can be selected as an example material. Graphite has a density of about 2.2 g/cc and a $^{13}$C-to-$^{12}$C ratio of about 1:99. If the goal is a $^{13}$C/$^{12}$C precision of about 1‰, counting statistics provides the estimated number of atoms of each isotope needed to achieve this precision as $^{12}$C=1.00×$10^7$ atoms and $^{13}$C=1.01×$10^6$ atoms. At a typical sputter rate of 1×$10^7$ atoms per second, a total sputter time of 10 seconds may be needed to achieve these totals. This provides a $^{12}$C counting error of 0.316‰ and a $^{13}$C counting error of 0.995‰. Combined, these values provide the target precision. Finally the volume of material sputtered can be calculated. The goal is to minimize this volume to give higher spatial resolution than is typically available.

Using the density of graphite, the theoretical required volume is only 8.3×$10^{-6}$ $\mu m^3$. This is a significant improvement over the typical $10^2$ $\mu m^3$. Improving efficiency factors for ion yield (to 1% or greater) and SIMS detection (to 0.1% or less) may further reduce this. Combined, these two factors may provide a 0.001% efficiency penalty. Thus, it can be estimated that the required volume is about 0.8 $\mu m^3$. Accordingly, significantly higher spatial resolution may be achievable than is now commonly used.

While the present techniques may be susceptible to various modifications and alternative forms, the exemplary embodiments discussed above have been shown only by way of example. However, it should again be understood that the

What is claimed is:

1. A method for microprobe analyses of isotope ratios in inhomogeneous matrices, comprising:
    selecting a plurality of matrix standards that have matrices that have a common characteristic with a sample matrix;
    running a bulk isotope analysis on each of the plurality of matrix standards to determine a bulk isotope ratio value for each of the plurality of matrix standards;
    running a plurality of microprobe analyses on each of the plurality of matrix standards to determine a plurality of microprobe isotope ratio values for each of the plurality of matrix standards;
    eliminating spurious values from the plurality of microprobe isotope ratio values;
    averaging the plurality of microprobe isotope ratio values for each of the plurality of matrix standards to create an average microprobe isotope ratio value associated with each of the plurality of matrix standards;
    plotting the bulk isotope ratio value for each of the plurality of matrix standards against the average microprobe isotope ratio value associated with each of the plurality of matrix standards to create a matrix corrected calibration curve; and
    running a microprobe analysis on a target region of the sample matrix and using the matrix corrected calibration curve to determine a matrix corrected isotope ratio, $\delta^n M$, for a selected element in the target region.

2. The method of claim 1, further comprising running a working standard during an analysis to correct isotope ratio measurements for instrumental mass fractionation (IMF).

3. The method of claim 1, further comprising:
    determining a plurality of matrix corrected isotope ratios for the sample matrix and creating a map of the matrix corrected isotope ratios of the sample matrix.

4. The method of claim 3, further comprising determining a quality of a reservoir core sample wherein the reservoir core sample comprises the sample matrix.

5. The method of claim 4, further comprising creating a map of grain coatings from the map of isotope ratios.

6. The method of claim 4, further comprising creating a map of cements from the map of isotope ratios.

7. The method of claim 3, wherein the map comprises $^{13}$C/$^{12}$C ($\delta^{13}$C) ratios.

8. The method of claim 7, further comprising determining an origin of carbon in minerals in the sample matrix.

9. The method of claim 3, wherein the map comprises $^{18}$O/$^{16}$O ($\delta^{18}$O) ratios.

10. The method of claim 9, further comprising determining a temperature of precipitation for minerals in the sample matrix.

11. The method of claim 3, wherein the map comprises $^{34}S/^{32}S$ ($\delta^{34}S$) ratios.

12. The method of claim 11, further comprising determining an origin of sulfur in minerals in the sample matrix.

13. The method of claim 3, further comprising determining grain provenance from the map of isotope ratios.

14. The method of claim 3, further comprising freezing the sample matrix on a cryogenic stage to solidify a fluid in the sample matrix prior to creating the map of isotope ratios of the sample matrix.

15. The method of claim 3, further comprising determining a connectivity of the sample matrix.

16. The method of claim 1, wherein a size of the target region is less than about 0.8 µm$^3$.

17. The method of claim 1, wherein the microprobe analysis is performed by secondary ion mass spectrometry (SIMS) and/or atom-probe mass spectrometry.

18. The method of claim 1, further comprising determining an isotope ratios ($\delta^n M$) of a fluid inclusion in the sample matrix by:
    solidifying the fluid inclusion using a low temperature; and
    running a microprobe analysis on the solidified fluid inclusion.

19. The method of claim 18, further comprising determining an isotope ratio of a component in a frozen brine in the solidified fluid inclusion.

20. The method of claim 1, further comprising determining a thermal, chemical and/or physical condition of the sample matrix based at least in part on the isotope ratio for the selected element.

21. The method of claim 20, further comprising:
    obtaining the sample matrix from a hydrocarbon reservoir; and
    producing hydrocarbons from the hydrocarbon reservoir based at least in part on the thermal, chemical and/or physical condition of the sample matrix.

22. The method of claim 1, wherein the isotope ratio is a $^{13}C/^{12}C$ isotope ratio ($\delta^{13}C$); and the method comprises determining a carbonate diagenesis based, at least in part, on the $\delta^{13}C$.

23. The method of claim 1, wherein the isotope ratio is a $^{18}O/^{16}O$ isotope ratio ($\delta^{18}O$).

24. The method of claim 23, further comprising determining a temperature of formation for a silica cement based, at least in part, on the $\delta^{18}O$.

25. The method of claim 23, further comprising:
    obtaining a record of formation temperature for the target region from a paleothermometer;
    determining a salinity of a fluid trapped in the target region; and
    determining a pore fluid evolution based at least in part on the $\delta^{18}O$, a fractionation factor for a mineral-water pair, and the formation temperatures.

26. The method of claim 1 wherein the isotope ratio is a $^{34}S/^{32}S$ isotope ratio ($\delta^{34}S$).

27. The method of claim 26, further comprising determining the probability of a sour gas condition based at least in part on the $\delta^{34}S$.

28. The method of claim 26, further comprising dating the time of precipitation of the target region based at least in part on a comparison of the $\delta^{34}S$ with a sulfur isotope variation in seawater over a period of time.

29. The method of claim 26, further comprising:
    obtaining the sample matrix from a hydrocarbon reservoir;
    determining an origin for $H_2S$ in the hydrocarbon reservoir by comparing the $\delta^{34}S$ of a gas in the reservoir to the $\delta^{34}S$ of the target region; and
    modifying exploration strategies based on a location of a sulfate source for the $H_2S$.

30. The method of claim 1, wherein the isotope ratio is a $^{87}Sr/^{86}Sr$ isotope ratio ($\delta^{86}Sr$) of the Ca-bearing cement; and the method may comprise determining an origin and precipitation time for a cement by comparing the $\delta^{86}Sr$ to a curve showing isotope variation over time.

31. A system for analyzing isotope variations in inhomogeneous matrices, comprising:
    an ion generator, wherein the ion generator is configured to generate ions from a target region of a sample;
    a particle detector, wherein the particle detector is configured to generate a signal that is proportional to the number of isotopes for a target element in the target region; and
    an analysis unit, comprising:
        an input system configured to process the signal from the particle detector to determine a count for two or more isotopes for the target element;
        a processor; and
        a memory device comprising code configured to direct the processor to:
            calculate an isotope ratio for the target element;
            project the isotope ratio onto a matrix corrected calibration curve,
            wherein the matrix corrected calibration curve comprises:
                selecting a plurality of matrix standards that have matrices that have a common characteristic with the sample;
                running a bulk isotope analysis on each of the plurality of matrix standards to determine a bulk isotope ratio value for each of the plurality of matrix standards;
                running a plurality of microprobe analyses on each of the plurality of matrix standards to determine a plurality of microprobe isotope ratio values for each of the plurality of matrix standards;
                eliminating spurious values from the plurality of microprobe isotope ratio values;
                averaging the plurality of microprobe isotope ratio values for each of the plurality of matrix standards to create an average microprobe isotope ratio value associated with each of the plurality of matrix standards;
                plotting the bulk isotope ratio value for each of the plurality of matrix standards against the average microprobe isotope ratio value associated with each of the plurality of matrix standards to create the matrix corrected calibration curve; and
            determine a matrix corrected value for the isotope ratio.

32. The system of claim 31, wherein the particle detector further comprises a sector field mass spectrometer.

33. The system of claim 31, wherein one of the particle detector and the ion generator further comprises an atom probe.

* * * * *